(12) United States Patent
Kobayashi et al.

(10) Patent No.: US 7,132,501 B2
(45) Date of Patent: Nov. 7, 2006

(54) POLYMERIZABLE COMPOSITION CONTAINING NOVEL CYCLIC SULFUR COMPOUND AND RESIN OBTAINED BY CURING THE POLYMERIZABLE COMPOSITION

(75) Inventors: Seiichi Kobayashi, Omuta (JP); Hiroyuki Morijiri, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/504,190

(22) PCT Filed: Feb. 27, 2003

(86) PCT No.: PCT/JP03/02189

§ 371 (c)(1),
(2), (4) Date: Aug. 11, 2004

(87) PCT Pub. No.: WO03/074588

PCT Pub. Date: Sep. 12, 2003

(65) Prior Publication Data
US 2005/0215757 A1    Sep. 29, 2005

(30) Foreign Application Priority Data
Mar. 1, 2002    (JP)    ............... 2002-55774

(51) Int. Cl.
*C08G 75/00* (2006.01)
(52) U.S. Cl. ............... 528/377; 528/378; 528/380
(58) Field of Classification Search ............ 528/377, 528/378, 380
See application file for complete search history.

(56) References Cited

U.S. PATENT DOCUMENTS

| | | | |
|---|---|---|---|
| 3,169,974 A | 2/1965 | Kohn | |
| 3,256,298 A | 6/1966 | Kilsheimer et al. | |
| 3,779,880 A | 12/1973 | Ohno et al. | |
| 4,277,554 A | 7/1981 | Eranian et al. | |
| 5,360,711 A | 11/1994 | Negoro et al. | |
| 5,374,668 A | 12/1994 | Kanemura et al. | |
| 5,807,975 A | 9/1998 | Amagai et al. | |
| 6,204,311 B1 | 3/2001 | Morijiri et al. | |
| 6,365,223 B1 | 4/2002 | Yoshimura et al. | |
| 6,472,495 B1 | 10/2002 | Yoshimura et al. | |
| 6,531,532 B1 | 3/2003 | Yoshimura et al. | |

FOREIGN PATENT DOCUMENTS

| | | |
|---|---|---|
| JP | 55-66909 A | 5/1980 |
| JP | 59-180544 A | 10/1984 |
| JP | 5-323545 | 12/1993 |
| JP | 5-323545 A | 12/1993 |
| JP | 9-110979 A | 4/1997 |
| JP | 11-256038 A | 9/1999 |
| JP | 11-322930 A | 11/1999 |
| JP | 2000-281787 A | 10/2000 |
| JP | 2001-2783 A | 1/2001 |
| JP | 2001-131257 A | 5/2001 |
| JP | 2002-40201 A | 2/2002 |
| JP | 2002-040201 A | 2/2002 |
| WO | 89/10575 A1 | 11/1989 |

*Primary Examiner*—Duc Truong
(74) *Attorney, Agent, or Firm*—Buchanan Ingersoll & Rooney PC

(57) ABSTRACT

A sulfur-containing compound has a structure represented by formula (1):

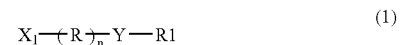

(wherein R1 represents a hydrogen atom, a reactive terminal group, a straight, branched or cyclic alkyl group having 1 to 10 carbon atoms and a reactive terminal group or its thia derivative thereof, an aryl group, or an aralkyl group; Y represents an oxygen atom, a sulfur atom, a selenium atom, or a tellurium atom; R represents a substituted or unsubstituted bivalent hydrocarbon group having 1 to 10 carbon atoms, which may be thianated; n represents an integer of 0 to 3; $X_1$ is substituted for any one of groups R2 to R7 of a partial structure represented by formula (2) in which the groups R2 to R7 other than the group substituted by $X_1$ are independently a hydrogen atom or a substituted or unsubstituted monovalent hydrocarbon group having 1 to 10 carbon atoms; and R1 is not a group having a (meth)acryl group when Y is an oxygen atom.)

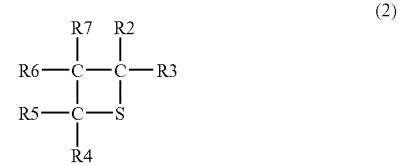

The compound has a high refractive index and high Abbe's number, and produces a resin having excellent impact resistance.

15 Claims, No Drawings

POLYMERIZABLE COMPOSITION CONTAINING NOVEL CYCLIC SULFUR COMPOUND AND RESIN OBTAINED BY CURING THE POLYMERIZABLE COMPOSITION

TECHNICAL FIELD

The present invention relates to a sulfur-containing cyclic compound which can be suitably used in the field of optical material resins and the like required to have a high refractive index and high transparency. The present invention also relates to a polymerizable composition containing the sulfur-containing cyclic compound, a resin and optical material produced by polymerization curing of the composition, and a method for producing a resin by curing the composition.

BACKGROUND ART

Plastic lenses have recently rapidly been widespread as optical materials for eyeglasses, camera lenses, and the like because the plastic lenses are lightweight and less broken and can be dyed, as compared with inorganic lenses.

The performances required for the plastic lenses include optical performances such as a high refractive index and a high Abbe's number, and physical and chemical properties such as high impact resistance, ease of dyeing, no problem about heat resistance, and a low specific gravity. The performances further include the property that the lens producing method and monomer compound used have safety of the human body and ease of handling.

Of these performances, high heat resistance and a low specific gravity are realized at a high level even by using an existing high-refractive-index plastic lens. An example of resins which are currently used for a variety of plastic lenses is a resin produced by radical polymerization of diethylene glycol bis(allyl carbonate) (referred to as "D. A. C" hereinafter). This resin has various properties such as excellent impact resistance, a light weight, excellent dyeing performance, good processability such as cutting ability, polishing ability, and the like, etc. However, this resin has a refractive index nd of as low as about 1.50, and thus the central thickness and edge thickness of a plastic lens are increased. Therefore, a resin having a higher refractive index is demanded for the plastic lenses.

Known examples of a resin having a higher refractive index than that of the D. A. C resin include sulfur atom-containing resins such as a polythiourethane resin, a sulfur-containing o-(meth)acrylate resin, and thio(meth)acrylate resin. The polythiourethane resin is a well-balanced resin having a high refractive index, excellent impact resistance, excellent dyeing performance, and the like. For other resins having a high refractive index and high Abbe's number, a method using a polyepisulfide compound is proposed (refer to, for example, Publication No. WO89/10575, Japanese Unexamined Patent Application Publication Nos. 9-110979 and 11-322930).

Also, a method of adding a known sulfur-containing compound to a polyepidithio compound or polyepisulfide compound is proposed for achieving a higher refractive index. However, the producing method and identification data for the compound are not described in examples, and a method of adding a known sulfur-containing compound to the polyepisulfide compound decreases the crosslinking property of a resin to decrease heat resistance. Therefore, this method has low practicability (refer to, for example, Japanese Unexamined Patent Application Publication Nos. 2000-281787, 2001-002783, and 2002-040201).

In the above-described method of adding a known sulfur-containing compound to the polyepisulfide compound, an example of compounds to be added is a monofunctional thietane compound. A typical known example of the thietane compound is methacryloyloxyalkylthietane which is used as a photopolymerizable compound for a photosensitive composition. This composition has a low refractive index and no transparency, and thus cannot be used for some optical applications required to have such a high refractive index as in the present invention (refer to, for example, Japanese Unexamined Patent Application Publication Nos. 55-066909 and 59-180544).

In the above-described conditions, the proposed method using the polyepisulfide compound having a high refractive index and high Abbe's number in a well-balanced state has been advanced to practical use. However, the method causes a handling problem due to the low thermal stability of the polyepisulfide compound in some cases. In order to solve the problem, a method for improving the thermal stability of the polyepisulfide compound is required, and various methods have been proposed. However, any one of the proposed methods is not satisfactory (refer to, for example, Japanese Unexamined Patent Application Publication No. 11-256038).

Furthermore, a resin produced by curing the polyepisulfide compound is brittle, and thus cannot be subjected to special processing such as two-point processing or the like, particularly, in the application to eyeglasses. Also, in some cases, there is the problem of cracking a lens in releasing after casting polymerization. Furthermore, in some of the applications to eyeglasses required to have safety, necessary physical properties are not sufficiently satisfied because of the low impact resistance of the resin. Therefore, various methods have been proposed for improving the resin, but any one of the methods is unsatisfactory (refer to, for example, Japanese Unexamined Patent Application Publication Nos. 2001-131257).

In a condition in which a plastic lens is required to have a higher refractive index and higher Abbe's number, it is greatly demanded to propose a novel compound which can be replaced with the polyepisulfide compound, which has a high refractive index and high Abbe's number, and which permits improvements in brittleness and impact resistance.

Therefore, the inventors conducted studies for improving the refractive index of a compound different from the polyepisulfide compound without decreasing the Abbe's number to provide a material complying with the requirements of a higher refractive index and higher Abbe's number.

DISCLOSURE OF THE INVENTION

As a result of intensive research for solving the above problems, the inventors found that a resin produced by curing a compound having a structure represented by formula (1), i.e., a sulfur-containing cyclic skeleton, has not only a high refractive index and high Abbe's number and excellent optical physical properties but also low brittleness and excellent impact resistance. The inventors also found that the compound is excellent in thermal stability as compared with the currently proposed polyepisulfide compound, leading to the achievement of the present invention.

The present invention includes the following matters:

[1] A sulfur-containing compound has a structure represented by formula (1).

   (1)

(wherein R1 represents a hydrogen atom, a reactive terminal group, a straight, branched or cyclic alkyl group having 1 to 10 carbon atoms and a reactive terminal group or its thia derivative, an aryl group, or an aralkyl group; Y represents an oxygen atom, a sulfur atom, a selenium atom, or a tellurium atom; R represents a substituted or unsubstituted bivalent hydrocarbon group having 1 to 10 carbon atoms, which may be thianated; n represents an integer of 0 to 3; $X_1$ is substituted for any one of groups R2 to R7 of a partial structure represented by formula (2) in which the groups R2 to R7 other than the group substituted by $X_1$ are independently a hydrogen atom or a substituted or unsubstituted monovalent hydrocarbon group having 1 to 10 carbon atoms; and R1 is not a group having a (meth)acryl group when Y is an oxygen atom.)

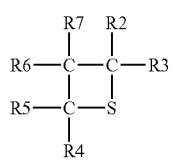   (2)

[2] The sulfur-containing cyclic compound [1] has a structure represented by formula (3).

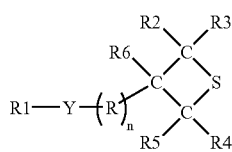   (3)

(wherein R1 represents a hydrogen atom, a reactive terminal group, a straight, branched or cyclic alkyl group having 1 to 10 carbon atoms and a reactive terminal group or its thia derivative, an aryl group, or an aralkyl group; R2 to R6 independently represent a hydrogen atom or a substituted or unsubstituted monovalent hydrocarbon group having 1 to 10 carbon atoms; R represents a substituted or unsubstituted divalent hydrocarbon group having 1 to 10 carbon atoms, which may be thianated; n represents an integer of 0 to 3; Y represents an oxygen atom, a sulfur atom, a selenium atom, or a tellurium atom; and R1 is not a group having a (meth)acryl group when Y is an oxygen atom.)

[3] The sulfur-containing cyclic compound [1] or [2] has a structure represented by formula (4).

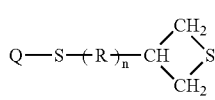   (4)

(wherein Q represents a hydrogen atom, a straight, branched or cyclic alkyl group having 1 to 10 carbon atoms and a reactive terminal group or its thia derivative, an aryl group, or an aralkyl group; R represents a substituted or unsubstituted divalent hydrocarbon group having 1 to 10 carbon atoms, which may be thianated; and n represents an integer of 0 to 3.)

[4] Any one of the sulfur-containing cyclic compounds [1] to [3] is 3-mercaptothietane, 3-(acryloylthio)thietane, 3-(methacryloylthio)thietane, 3-(2,3-epithiopropylthio)thietane, 3-(allylthio)thietane, 3-(isocyanatomethylthio)thietane, 3-(aminoethylthio)thietane, or 3-(isothiocyanatoethylthio)thietane.

[5] Any one of the sulfur-containing compounds [1] to [3] has a structure represented by formula (5).

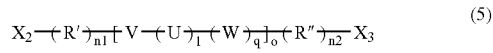   (5)

(wherein R' and R" independently represent a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; each of V and W represents an oxygen atom, a sulfur atom, a selenium atom, or a tellurium atom; l represents an integer of 0 to 2; o represents an integer of 1 to 4; n1 and n2 independently represent an integer of 0 to 3; q represents an integer of 0 or 1; $X_2$ is substituted for any one of groups R9 to R14 of a partial structure represented by formula (6), and $X_3$ is substituted for any one of groups R15 to R20 of the partial structure represented by formula (6) in which the groups R9 to R20 other than the groups substituted by $X_2$ and $X_3$ are independently a hydrogen atom or a substituted or unsubstituted monovalent hydrocarbon group having 1 to 10 carbon atoms.)

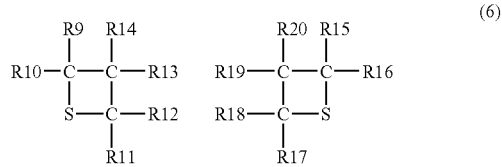   (6)

[6] Any one of the sulfur-containing cyclic compounds [1] to [3] and [5] is represented by formula (7).

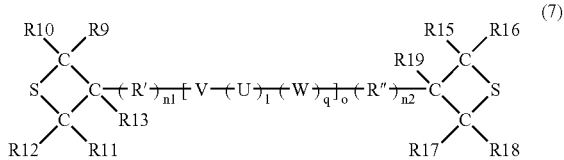   (7)

(wherein R9 to R19 independently represent a hydrogen atom, a substituted or unsubstituted monovalent hydrocarbon group having 1 to 10 carbon atoms; R' and R" independently represent a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; each of V and W represents an oxygen atom, a sulfur atom, a selenium atom, or a tellurium atom; l represents an integer of 0 to 2; o represents an integer of 1 to 4; n1 and n2 independently represent an integer of 0 to 3; and q represents an integer of 0 or 1.)

[7] Any one of the sulfur-containing cyclic compounds [1] to [3] or [5] and [6] is represented by formula (8).

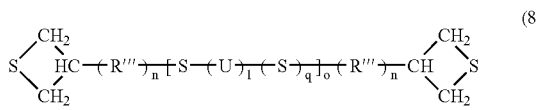

(wherein R''' represents a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; l represents an integer of 0 to 2; o represents an integer of 1 to 4; n represents an integer of 0 to 3; and q represents an integer of 0 or 1.)

[8] Any one of the sulfur-containing cyclic compounds [1] to [3] or [5] to [7] is bis(3-thietanyl) disulfide, bis(3-thietanyl) sulfide, bis(3-thietanylthio) methane, bis(3-thietanylthiomethyl) sulfide, 1,4-bis(3-thietanylthiomethyl) benzene, 1,3-bis(thietanylthiomethyl) benzene, 1,2-bis(thietanylthiomethyl) benzene, 2,5-bis(3-thietanylthiomethyl)-1,4-dithiane, 1,3-bis(3-thietanylthio) propane-1-one, or 1,3-bis(3-thietanylthio)propane-1-one-2-methyl.

[9] Any one of the sulfur-containing cyclic compounds [1] to [8] is derived from 3-thiethanol and/or 3-halogenothietane and/or 3-mercaptothietane.

[10] A polymerizable composition containing any one of the compounds [1] to [9].

[11] A resin is produced by curing the polymerizable composition [10].

[12] An optical material comprises the resin [11].

[13] A method for producing a resin comprises cast-polymerizing the polymerizable composition [11].

[14] A method for producing a resin comprises curing a resin by using the polymerizable composition [10] as a curing catalyst, and at least one compound selected from boron trihalides and complexes thereof, trihalogenomethane sulfonic acids and esters and anhydrides thereof.

[15] A method for producing a resin comprises curing a resin by using the polymerizable composition [10] as a resin modifier, and at least one compound selected from compounds each having at least one SH group and/or NH group and/or NH₂ group.

BEST MODE FOR CARRYING OUT THE INVENTION

The present invention will be described in detail below.

In the present invention, a sulfur-containing cyclic compound means a compound having at least one partial structure represented by formula (9).

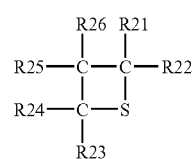

(wherein each of R21 to R26 represents a hydrogen atom or a substituted or unsubstituted hydrocarbon group having 1 to 10 carbon atoms.)

Namely, the sulfur-containing cyclic compound is represented by formula (1).

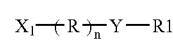

(wherein R1 represents a hydrogen atom, a reactive terminal group, a straight, branched or cyclic alkyl group having 1 to 10 carbon atoms and a reactive terminal group or its thia derivative, an aryl group, or an aralkyl group; Y represents an oxygen atom, a sulfur atom, a selenium atom, or a tellurium atom; R represents a substituted or unsubstituted bivalent hydrocarbon group having 1 to 10 carbon atoms, which may be thianated; n represents an integer of 0 to 3; and X₁ is substituted for any one of groups R2 to R7 of a partial structure represented by formula (2) in which the groups R2 to R7 other than the group substituted by X₁ are independently a hydrogen atom or a substituted or unsubstituted monovalent hydrocarbon group having 1 to 10 carbon atoms.)

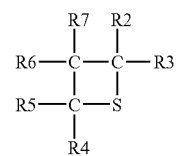

Substituted or unsubstituted monovalent hydrocarbon groups represented by R2 to R7 and each having 1 to 10 carbon atoms include a straight, branched or cyclic alkyl group, a straight, branched or cyclic alkenyl group, an aryl group and an aralkyl group. Each of R2 to R7 is preferably a hydrogen atom or a straight, branched or cyclic alkyl group having 1 to 10 carbon atoms, and more preferably a hydrogen atom.

Examples of a substituted or unsubstituted divalent hydrocarbon group represented by R and having 1 to 10 carbon atoms include a straight, branched or cyclic alkylene group, a straight, a branched or cyclic alkenyl group, an arylene group, and aralkylene group.

Y represents any one of an oxygen atom, a sulfur atom, a selenium atom, and a tellurium atom, and Y is preferably a sulfur atom.

R1 represents a hydrogen atom, a reactive terminal group, a straight, branched or cyclic alkyl group having 1 to 10 carbon atoms and a reactive terminal group or a thia derivative thereof, an aryl group, or an aralkyl group. Examples of a reactive terminal group include polymerizable reactive groups such as a thietanyl group, an episulfide group, an alkyleneoxido(thio) group, a —Z—H group (wherein Z represents an oxygen atom, a sulfur atom, a selenium atom, or a tellurium atom), an iso(thio)cyanato group, an amino group, a (thio)(meth)acryl group, an alkenyl(thio) group, and the like. Preferred examples include a thietanyl group, a thietanylthio group, an oxetanyl group, an oxetanylthio group, an episulfide group, an epoxy group, a mercapto group, a hydroxyl group, an iso(thio)cyanato group, an amino group, a (thio)(meth)acryl group, a vinyl(thio) group, an allyl(thio) group, and an isopropenyl group. Particularly, a thietanyl group, a thietanylthio group, an episulfide group, a mercapto group, an isothiocyanato group, a thio(meth)acryl group, a vinylthio group, and an allylthio group are preferred. The number of the reactive terminal group is not limited to one, and a plurality of reactive terminal groups may be contained. When R1 is a reactive terminal group, R1 is preferably a thietanyl group, an oxetanyl group, an episulfide group, an epoxy group, a vinyl group, an allyl group, an acryl group, or a methacryl group.

The compound represented by formula (1) is preferably a compound represented by formula (3) in which R7 is substituted by $X_1$.

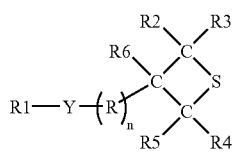

(3)

(wherein R2 to R6 independently represent a hydrogen atom or a substituted or unsubstituted monovalent hydrocarbon group having 1 to 10 carbon atoms; R represents a substituted or unsubstituted divalent hydrocarbon group having 1 to 10 carbon atoms, which may be thianated; n represents an integer of 0 to 3; Y represents a sulfur atom, a selenium atom, or a tellurium atom; and R1 represents a hydrogen atom, a reactive terminal group, a straight, branched or cyclic alkyl group having 1 to 10 carbon atoms and a reactive terminal group or a thia derivative thereof, an aryl group, or an aralkyl group.)

The compound represented formula (3) is preferably a 3-thietane compound represented by formula (4) in which Y is a sulfur atom.

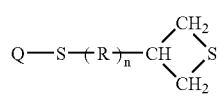

(4)

(wherein Q represents a hydrogen atom, a straight, branched or cyclic alkyl group having 1 to 10 carbon atoms and a reactive terminal group or a thia derivative thereof, an aryl group, or an aralkyl group; R represents a substituted or unsubstituted divalent hydrocarbon group having 1 to 10 carbon atoms, which may be thianated; and n represents an integer of 0 to 3.)

In the present invention, a compound having two or more structures represented by formula (8) is preferred for providing a resin having a high refractive index and excellent optical physical properties. Namely, a sulfur-containing cyclic compound represented by formula (5) is preferred.

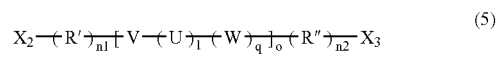

(5)

(wherein R' and R" independently represent a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; each of V and W represents an oxygen atom, a sulfur atom, a selenium atom, or a tellurium atom; l represents an integer of 0 to 2; o represents an integer of 1 to 4; n1 and n2 independently represent an integer of 0 to 3; q represents an integer of 0 or 1; $X_2$ is substituted for any one of groups R9 to R14 of a partial structure represented by formula (6), and $X_3$ is substituted for any one of groups R15 to R20 of the partial structure represented by formula (6) in which the groups R9 to R20 other than the groups substituted by $X_2$ and $X_3$, respectively, are independently a hydrogen atom or a substituted or unsubstituted monovalent hydrocarbon group having 1 to 10 carbon atoms.)

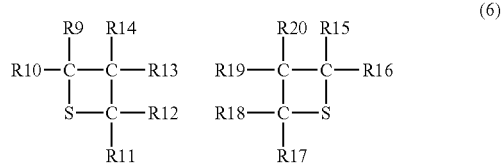

(6)

In formula (6), R9 to R20 are defined to have the same meaning as R1 to R6 in formula (1), and R' and R" are defined to have the same meaning as R in formula (1).)

In formula (6), preferably, R14 is substituted by $X_2$, and R20 is substituted by $X_3$, as shown by a compound represented by formula (7).

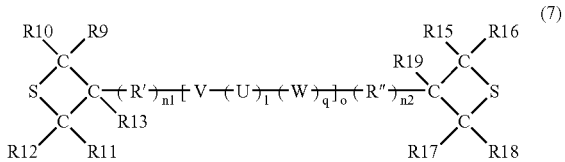

(7)

(wherein R9 to R19 independently represent a substituted or unsubstituted monovalent hydrocarbon group having 1 to 10 carbon atoms; R' and R" independently represent a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; each of V and W represents an oxygen atom, a sulfur atom, a selenium atom, or a tellurium atom; l represents an integer of 0 to 2; o represents an integer of 1 to 4; n1 and n2 independently represent an integer of 0 to 3; and q represents an integer of 0 or 1.)

Each of V and W represents any one of an oxygen atom, a sulfur atom, a selenium atom, and a tellurium atom, and preferably a sulfur atom.

U is preferably a straight, branched or cyclic alkylene group having 1 to 10 carbon atoms, an arylene group having 6 to 10 carbon atoms, or an aralkylene group having 7 to 10 carbon atoms, and a methylene group of an alkyl component in an alkylene or aralkylene group may be partially thianated with sulfur. Examples of such groups include divalent groups derived from straight alkanes such as methane, ethane, propane, butane, and the like; divalent groups derived from branched alkanes such as isopropane, sec-butane, tert-butane, sec-pentane, neo-pentane, and the like; divalent groups derived from cyclic alkanes such as cyclopentane, cyclohexane, and the like; divalent groups derived from straight or branched thiaalkanes such as 3-thiapentane, 4-thiahexane, 3,6-dithiaoctane, 3,6,9-trithiaundecane, and the like; divalent groups derived from cyclic thiaalkanes such as 1,4-dithiane, 1,3-dithiane, 1,3-dithiolane, 1,3-dithietane, and the like; divalent groups derived from unsubstituted or alkyl-substituted benzenes such as benzene, toluene, xylene, and the like; divalent groups derived from aromatic heterocycles such as thiophene and the like.

U may be substituted by the reactive terminal group or an alkylenesulfido(thio) group except an episulfide group. Particularly, U may have 1 to 3 thietanyl groups or thietanylthio groups as substituents. Namely, the present invention includes tri- or higher-functional sulfur-containing cyclic compounds.

l represents an integer of 0 to 2. For example, when U is phenylene, and l is 2, the compound contains biphenylene.

Particularly, the compound represented by formula (7) preferably has a structure represented by formula (8).

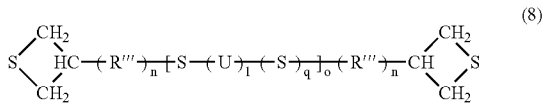
(8)

(wherein R''' is defined to have the same meaning as R' and R'', U, l, o, and q are defined to have the same meaning as described above, and n represents an integer of 0 to 3.)

Examples of the compound having the structure represented by formula (8) include chain aliphatic 3-thietanyltio compounds such as 1,1-bis(3-thietanylthio)methane, 1,2-bis(3-thietanylthio)ethane, 1,2-bis(3-thietanylthio)propane, 1,3-bis(3-thietanylthio)propane, 1,3-bis(3-thietanylthio)-2-methylpropane, 1,4-bis(3-thietanylthio)butane, 1,4-bis(3-thietanylthio)-2-methylbutane, 1,3-bis(3-thietanylthio)butane, 1,5-bis(3-thietanylthio)pentane, 1,5-bis(3-thietanylthio)-2-methylpentane, 1,5-bis(3-thietanylthio)-3-thiapentane, 1,6-bis(3-thietanylthio)hexane, 1,6-bis(3-thietanylthio)-2-methylhexane, 3,8-bis(3-thietanylthio)-3,6-dithiaoctane, 1,2,3-tris(3-thietanylthio)propane, 2,2-bis(3-thietanylthio)-1,3-bis(3-thietanylthio)propane, 2,2-bis(3-thietanylthio)-1-(3-thietanylthio)butane, 1,5-bis(3-thietanylthio)-2-(3-thietanylthiomethyl)-3-thiapentane, 1,5-bis(3-thietanylthio)-2,4-bis(3-thietanylthiomethyl)-3-thiapentane, 1-(3-thietanylthio)-2,2-bis(3-thietanylthiomethyl)-4-thiahexane, 1,5,6-tris(3-thietanylthio)-4-(3-hietanylthiomethyl)-3-thiahexane, 1,8-bis(3-thietanylthio)-4-(3-thietanylthiomethyl)-3,6-dithiaoctane, 1,8-bis(3-thietanylthio)-4,5-bis(3-thietanylthiomethyl)-3,6-dithiaoctane, 1,8-bis(3-thietanylthio)-4,4-bis(3-thietanylthiomethyl)-3,6-dithiaoctane, 1,8-bis(3-thietanylthiomethyl)-3,6-dithiaoctane, 1,8-bis(3-thietanylthio)-2,4,5-tris(3-thietanylthiomethyl)-3,6-dithiaoctane, 1,1,1-tris[[2-(3-thietanylthio)ethyl]thiomethyl]-2-(3-thietanylthio)ethane, 1,1,2,2-tetrakis[[2-(3-thietanylthio)ethyl]thiomethyl]ethane, 1,11-bis(3-thietanylthio)-4,8-bis(3-thietanylthiomethyl)-3,6,9-trithiaundecane, 1,11-bis(3-thietanylthio)-4,7-bis(3-thietanylthiomethyl)-3,6,9-trithiaundecane, 1,11-bis(3-thietanylthio)-5,7-bis(3-thietanylthiomethyl)-3,6,9-trithiaundecane, 1,1,3,3-tetrakis(3-thietanylthiomethylthio)propane, 1,1,2,2-tetrakis(3-thietanylthiomethylthio)ethane, 3-(3-thietanylthiomethyl)-1,5-di(3-thietanylthio)-2,4-dithiapentane, and the like; cyclic aliphatic 3-thietanylthio compounds such as 1,3-bis(3-thietanylthio)cyclohexane, 1,4-bis(3-thietanylthio)cyclohexane, 1,3-bis(3-thietanylthiomethyl)cyclohexane, 1,4-bis(3-thietanylthiomethyl)cyclohexane, 2,5-bis(3-thietanylthiomethyl)-1,4-dithiane, 4,6-bis(3-thietanylthiomethyl)-1,3-dithiane, 4,5-bis(3-thietanylthiomethyl)-1,3-dithiolane, 2,4-bis(3-thietanylthiomethyl)-1,3-dithietane, 2,5-bis[[2-(3-thietanylthio)ethyl]thiomethyl]-1,4-dithiane, 2,5-bis(3-thietanylthiomethyl)-2,5-dimethyl-1,4-dithiane, 2-bis(3-thietanylthio)methyl-1,3-dithiolane, and the like; aromatic 3-thietanylthio compounds such as 1,2-bis(3-thietanylthio)benzene, 1,3-bis(3-thietanylthio)benzene, 1,4-bis(3-thietanylthio)benzene, 1,2-bis(3-thietanylthiomethyl)benzene, 1,3-bis(3-thietanylthiomethyl)benzene, 1,4-bis(3-thietanylthiomethyl)benzene, bis[4-(3-thietanylthio)phenyl]methane, 2,2-bis[4-(3-thietanylthio)phenyl]propane, bis[4-(3-thietanylthio)phenyl]sulfide, bis[4-(3-thietanylthio)phenyl]sulfone, 4,4'-bis(3-thietanylthio)biphenyl, and the like; asymmetric compounds such as 1,3-bis(3-thietanylthio)propane-1-one, 1,3-bis(3-thietanylthio)-2-methylpropane-1-one, and the like. However, the compounds are not limited to these examples. of these compound examples, preferred compounds include 1,1-bis(3-thietanylthio)methane, 1,2-bis(3-thietanylthio)ethane, 1,2,3-tris(3-thietanylthio)propane, 1,8-bis(3-thietanylthio)-4-(3-thietanylthiomethyl)-3,6-dithiaoctane, 1,11-bis (3-thietanylthio)-4,8-bis (3-thietanylthiomethyl)-3,6,9-trithiaundecane, 1,11-bis(3-thietanylthio)-4,7-bis(3-thietanylthiomethyl)-3,6,9-trithiaundecane, 1,11-bis(3-thietanylthio)-5,7-bis(3-thietanylthiomethyl)-3,6,9-trithiaundecane, 2,5-bis(3-thietanylthiomethyl)-1,4-dithiane, 2,5-bis[[2-(3-thietanylthio)ethyl]thiomethyl]-1,4-dithiane, 2,5-bis(3-thietanylthiomethyl)-2,5-dimethyl-1,4-dithiane, 4,5-bis(3-thietanylthiomethyl)-1,3-dithiolane, 2,4-bis(3-thietanylthiomethyl)-1,3-dithietane, and 2-bis(3-thietanylthio)methyl-1,3-dithiolane. More preferred compounds include bis(3-thietanylthio)methane, bis(3-thietanylthiomethyl)sulfide, and 2-bis(3-thietanylthio)methyl-1,3-dithiolane.

The sulfur-containing cyclic compound represented by formula (1) of the present invention can be derived from, for example, a 3-hydroxy(alkyl)thietane compound represented by formula (10).

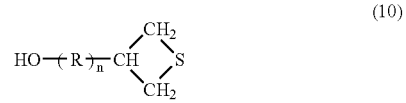
(10)

(wherein R represents a substituted or unsubstituted divalent hydrocarbon group having 1 to 10 carbon atoms, which may be thianated, and n represents an integer of 0 to 3.)

Examples of a compound having a structure represented by formula (10) include alkylthietane compounds such as 3-thietanol, 3-hydroxymethylthietane, 3-hydroxyethylthietane, 3-hydroxypropylthietane, 3-hydroxyisopropylthietane, and the like; sulfur-containing hydroxythietane compounds such as 3-hydroxyethylthiothietane, and the like. However, the compounds are not limited to these examples.

A typical example is 3-thietanol that can easily be synthesized by a known method. For example, epihalohydrin and an alkali may be simultaneously charged in an alcohol or water saturated with dissolved hydrogen sulfide. As the alcohol, any alcohol may be used as long as hydrogen sulfide can be dissolved therein. However, methanol having high dissolving power is preferred. As the epihalohydrin, epichlorohydrin and epibromohydrin are preferred. As the alkali, either an inorganic or organic alkali may be used. Preferred examples of the alkali include alkali metal or alkali earth metal hydroxides, alkali metal or alkali earth metal carbonates, alkali metal or alkali earth metal bicarbonates, ammonia, tertiary amines, secondary amines, primary amines, metal alkoxides, and the like. Another method may be used, in which 1-chloro-3-mercaptopropane-2-ol is reacted with an alkali in the absence of presence of a solvent such as water, an alcohol, or the like.

The 3-hydroxy(alkyl)thietane compound including 3-thiethanol having the structure represented by formula (10) can be converted into a 2-halogeno(alkyl)thietane compound having a structure represented by formula (11) using a halogenating agent or the like.

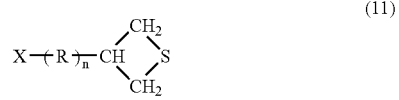

(11)

(wherein X represents a halogen atom such as chlorine, bromine, iodine, or the like, R represents a substituted or unsubstituted straight, branched or cyclic hydrocarbon group having 1 to 10 carbon atoms, and n represents an integer of 0 to 3.)

Preferred examples of the halogenating agent include thionyl chloride, phosphorus trichloride, hydrochloric acid, hydrogen chloride, phosphorus tribromide, hydrobromic acid, hydrogen bromide, chlorine, bromine, and the like. However, the halogenating agents are not limited to these examples. Although the solvent used in the reaction depends upon the type of the halogenating agent used, the solvent need not be used in the reaction, or any solvent may be used as long as it does not inhibit halogenation and does not react with the halogenating agent. Although the reaction temperature also depends upon the type of the halogenating agent used, good results are obtained with the reaction temperature of −30° C. to 50° C. in some cases, and the reaction temperature is preferably −10° C. to 30° C.

Examples of the compound having the structure represented by formula (11) include halogeno(alkyl)thietane compounds such as 3-chlorothietane, 3-chloromethylthietane, 3-chloroethylthietane, 3-chloropropylthietane, 3-chloroisopropylthietane, and the like; compounds having bromo groups substituted for the chloro groups of the chloro(alkyl) thietane compounds; compounds having iodo groups substituted for the chloro groups of the chloro(alkyl)thietane compounds; sulfur-containing halogeno(alkyl)thietane compounds such as 3-chloroethylthiothietane, and the like. The compounds are not limited to these examples.

Of compounds (formula (5)) each having two or more structures represented by formula (9), a compound represented by formula (7) having at least two thietanyl groups can be synthesized by, for example, the following method.

The 3-halogeno(alkyl)thietane compound having the structure represented by formula (11) is reacted with a alkali sulfide such as sodium sulfide, disodium disulfide, disodium trisulfide, disodium tetrasulfide, potassium sulfide, dipotassium disulfide, dipotassium trisulfide, dipotassium tetrasulfide, or the like to synthesize bis(3-thietanylalky) sulfide, bis(3-thietanylalkyl) disulfide, bis(3-thietanylalkyl) trisulfide, bis(3-thietanylalkyl) tetrasulfide, or the like. Therefore, bis(3-thietanyl) sulfide, bis(3-thietanyl) disulfide, bis(3-thietanyl) trisulfide, bis(3-thietanyl) tetrasulfide, or the like can be synthesized from 3-halogenothietane. Although the solvent used for the reaction depends upon the type of a compound to be synthesized, no solvent or the use of a solvent which can dissolve the reaction product, such as a hydrocarbon compound, an aromatic compound, a halogenated compound, an ester compound, an ether compound, a ketone compound, or the like produces good results in some cases. Although benzene, toluene, diethyl ether, methyl ethyl ketone, methyl isobutyl ketone, or the like is preferably used, the solvents are not limited to these compounds. Although the reaction temperature also depends upon the type of the compound to be synthesized, the reaction temperature of −30° C. to 100° C. generally produces good results in some cases. The reaction temperature is preferably −10° C. to 50° C., and more preferably 0° C. to 30° C.

The target sulfur-containing cyclic compound can be synthesized by reacting 3-halogeno(alkyl)thietane with a known polythiol compound. In an example of a synthetic method, 3-halogeno(alkyl)thietane is mixed with a polythiol compound in the presence or absence of the solvent, and an alkali such as an inorganic alkali, a metal alkoxide, an organic amine, or the like is added to the resultant mixture. Another example comprises mixing and reacting 3-halogeno (alkyl)thietane with a solution of a metal salt of a polythiol compound in which its thiol groups are reacted with an inorganic alkali or metal alkoxide. The quantitative ratio of 3-halogeno(alkyl)thietane to the polythiol compound required for the reaction, i.e., the ratio of (halogeno groups of 3-halogeno(alkyl)thietane)/(thiol groups of the polythiol compound), is theoretically 1. However, considering the reaction rate and economy, the quantitative ratio is 0.5 to 2, preferably 0.8 to 1.5, and more preferably 0.9 to 1.2. Although the solvent used for the reaction depends upon the type of the compound to be synthesized, no solvent or the use of a solvent which can dissolve the reaction product, such as an inorganic or organic hydrocarbon compound, an aromatic compound, a halogenated compound, an ester compound, an ether compound, a ketone compound, or the like produces good results in some cases. Although benzene, toluene, diethyl ether, methyl ethyl ketone, methyl isobutyl ketone, or the like is particularly preferred, the solvents are not limited to these compounds. Although the reaction temperature also depends upon the type of the compound to be synthesized, the reaction temperature of −50° C. to 100° C. generally produces good results in some cases. The reaction temperature is preferably −30° C. to 50° C., and more preferably −10° C. to 30° C.

As the polythiol compound used as a raw material, any one of known polythiol compounds may be used. However, preferred examples include aliphatic thiols such as 1,1-methanedithiol, 1,2-ethanedithiol, 1,2-propanedithiol, 1,3-propanedithiol, 2,2-propanedithiol, 1,4-butanediol, 1,2,3-trimercaptopropane, tetrakis(mercaptomethyl)methane, 1,2-dimercaptocyclohexane, bis(1-mercaptomethyl) sulfide, bis (2-mercaptoethyl) sulfide, 2,3-dimercapto-1-propanol, 1,3-dimercapto-2-propanol, ethyleneglycol bis(3-mercaptopropionate), diethyleneglycol bis(3- mercaptopropionate), diethyleneglycol bis(2-mercaptoglycolate), pentaerythritol tetrakis(2-mercaptothioglycolate), pentaerythritol tetrakis(3-mercaptopropionate), trimethylolpropane tris(2-mercaptothioglycolate), trimethylolpropane tris(3-mercaptopropionate), 1,1,1-trimethylmercaptoethane, 1,1,1-trimethylmercaptopropane, 2,5-dimercaptomethyl thiophene, 4-mercaptomethyl-1,8-dimercapto-3,6-dithiaoctane, 2,5-dimercaptomethyl-1,4-dithiane, 2,5-bis[(2-mercaptoethyl)thiomethyl]-1,4-dithiane, 1,3-cyclohexanedithiol, 1,4-cyclohexanedithiol, 4,8-dimercaptomethyl-1,11-mercapto-3,6,9-trithiaundecane, 4,7-dimercaptomethyl-1,11-mercapto-3,6,9-trithiaundecane, 5,7-dimercaptomethyl-1,11-mercapto-3,6,9-trithiaundecane, 1,1,3,3-tetrakis(mercaptomethylthio)propane, 1,1,2,2-tetrakis(mercaptomethylthio)ethane, 3-mercaptomethyl-1,5-dimercapto-2,4-dithiapentane, tris(mercaptomethylthio) methane, 4,6-dimercapto-1,3-dithiane, and the like; aromatic thiols such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis (mercaptomethyl)benzene, 2,2'-dimercaptobiphenyl, 4,4'-dimercaptobiphenyl, bis(4-mercaptophenyl)methane, bis(4-mercaptophenyl) sulfide, bis(4-mercaptophenyl) sulfone, 2,2-bis(4-mercaptophenyl)propane, 1,2,3-trimercaptobenzene, 1,2,4-trimercaptobenzene, 1,2,5-trimercaptobenzene, and the like. However, the polythiol compounds are not limited to theses examples.

A halogen atom of 3-halogeno(alkyl)thietane can be converted to a mercapto group by a substitution reaction. Known methods for the substitution reaction include a reaction using thiourea, a method using an alkali metal hydrosulfide or alkali metal sulfide such as sodium hydrosulfide, potassium hydrosulfide, sodium sulfide, potassium sulfide, or the like, a method using a metal polysulfide such as sodium polysulfide, potassium polysulfide, or the like, a method using an alkali metal carbonate such as sodium trithiocarbonate, potassium trithiocarbonate, or the like, a method using potassium xanthogenate, a method using a Bunte salt, and the like. In the method using a thiocyanate, thiourea, triphenylphosphine sulfide, or the like, preferably a thiocyanate or thiourea, as a thianation agent, 3-halogeno (alkyl)thietane is reacted with the thianation agent in at least one solvent selected from water, an alcohol, a ketone, an ester, and the like to form an isothiuronium salt. The same alkali as described above is added to a solution containing the isothiuronium salt or the isolated isothiuronium salt and reacted therewith to synthesize 3-mercapto(alkyl)thietane having a structure represented by formula (12).

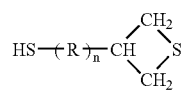

(12)

(wherein R represents a substituted or unsubstituted divalent hydrocarbon group having 1 to 6 carbon atoms, and n represents an integer of 0 to 3).

Preferred examples of the alkali used in the reaction include ammonia, sodium hydroxide, potassium hydroxide, calcium hydroxide, sodium carbonate, potassium carbonate, ammonium carbonate, and aqueous solutions of these alkalis. Although the solvent used for adding the alkali depends upon the type of a compound to be synthesized, the solvent need not be used, or any solvent may be used as long as it does not inhibit the reaction with the alkali and does not react with the alkali. Although the reaction temperature also depends upon the type of the compound to be synthesized, the reaction temperature of −30° C. to 100° C. generally produces good results in some cases. The reaction temperature is preferably −10° C. to 80° C., and more preferably 10° C. to 60° C.

3-mercapto(alkyl)thietane can be reacted with various halogenated hydrocarbon compounds to synthesize the above-described various thietane compounds. A method for reacting 3-mercapto(alkyl)thietane with a halogenated hydrocarbon compound comprises adding a metal alkoxide to a composition containing the halogenated hydrocarbon compound and 3-mercapto(alkyl)thietane, and the method produces good results in some cases. Another method comprises reacting an alkali metal salt or metal alkoxide with 3-mercapto(alkyl)thietane to form a salt, and thus reacting the salt with the halogenated hydrocarbon compound, and the method also produces good results in some cases. Although the reaction solvent used in the methods depends upon the type of a compound to be synthesized, the solvent need not be used, or any solvent may be used as long as it does not inhibit the reaction of the alkali metal salt or metal alkoxide, 3-mercapto(alkyl)thietane and the halogenated hydrocarbon compound and does not react with the alkali metal salt or metal alkoxide. Although the reaction temperature also depends upon the type of the compound to be synthesized, the reaction temperature of −70° C. to 50° C. generally produces good results in some cases, and the reaction temperature is preferably −50° C. to 50° C.

As the halogenated hydrocarbon compound used in the reaction, any one of known halogenated hydrocarbon compounds may be used. Preferred examples of the halogenated hydrocarbon compound include aliphatic halogenated hydrocarbon compounds such as 1,1-dichloromethane, 1,2-dichloroethane, 1,2-dichloropropane, 1,3-dichloropropane, 2,2-dichloropropane, 1,4-dichlorobutane, 1,2,3-trichloropropane, tetrakis(chloromethyl)methane, 1,2-dichlorocyclohexane, bis(1-chloromethyl) sulfide, bis(2-chloroethyl) sulfide, 2,3-dichloro-1-propanol, 1,1,1-trimethylchloroethane, 1,1,1-trimethylchloropropane, 2,5-dichloromethylthiophane, 4-chloromethyl-1,8-dichloro-3,6-dithiaoctane, 2,5-dichloromethyl-1,4-dithiane, 2,5-bis[(2-chloroethyl)thiomethyl]-1,4-dithiane, 1,3-dichlorocyclohexane, 1,4-dichlorocyclohexane, 4,8-dichloromethyl-1,11-chloro-3,6,9-trithiaundecane, 4,7-dichloromethyl-1,11-chloro-3,6,9-trithiaundecane, 5,7-dichloromethyl-1,11-chloro-3,6,9-trithiaundecane, and the like, and compounds in which chloro groups of these compounds are substituted by bromo or iodo groups; aromatic halogenated hydrocarbon compounds such as 1,2-dichlorobenzene, 1,3-dichlorobenzene, 1,4-dichlorobenzene, 1,2-bis(chloromethyl)benzene, 1,3-bis (chloromethyl)benzene, 1,4-bis(chloromethyl)benzene, 2,2'-dichlorobiphenyl, 4,4'-dichlorobiphenyl, bis(4-chlorophenyl)methane, bis(4-chlorophenyl) sulfide, bis(4-chlorophenyl) sulfone, 2,2-bis(4-chlorophenyl)propane, 1,2,3-trichlorobenzene, 1,2,4-trichlorobenzene, 1,2,5-trichlorobenzene, and the like, and compounds having bromo or iodo groups substituted for the chloro groups of these compounds. However, the halogenated hydrocarbon compounds are not limited to these examples.

Also, a compound having another functional group which can react with a mercapto group, for example, an aldehyde, an acetal, a ketone, a ketal, an epoxy, an episulfide, an olefin, an iso(thio)cyanate, a thiol, an acid halide, an acid anhydride, or the like, may be reacted with a 3-mercapto(alkyl) thietane compound to directly synthesize a compound having the structure represented by formula (4) in which the reactive terminal group is a thietanyl group. Examples of aldehydes, acetals and ketones include aldehydes such as formaldehyde, acetoaldehyde, propionaldehyde, benzaldehyde, glyoxal, malonaldehyde, 2-thiophenaldehyde, methylbenzaldehyde, phthalaldehyde, and the like; acetal compounds of these aldehyde compounds; ketones such as acetone, acetophenone, benzophenone, methyl ethyl ketone, cyclopentanone, cyclohexanedione, and the like; ketals of these ketones; and the like. Examples of epoxys, episulfides, olefins, iso(thio)cyanates, thiols, acid halides, and acid anhydrides include the compounds having functional groups, which are described above and below. However, the compounds are not limited to these examples.

Furthermore, a thietane compound having a disulfide bond can be synthesized by inter-molecular oxidation of the 3-mercapto(alkyl)thietane compound. Therefore, bis(3-thietanyl) disulfide can be synthesized by oxidation of the 3-mercaptothietane. Similarly, bis(3-thietanylalkyl) disulfide can be synthesized by using a 3-mercapto(alkyl)thietane compound. As the oxidizing agent used for the oxidation reaction, any oxidizing agent usually used for oxidizing a mercapto group to form a disulfide bond may be used. Examples of the oxidizing agent include oxygen, hydrogen peroxide and an aqueous solution thereof, hypohalogenous acid salts such as sodium hypochlorite, and the like, and aqueous solutions of these salts; persulfates such as ammonium persulfate, and the like, aqueous solutions of these persulfates; halogens such as iodine, bromine, chlorine, and the like; sulfuryl chloride; iron (III) chloride; sulfoxide compounds such as dimethylsulfoxide, and the like; nitrogen oxide; and the like. However, the oxidizing agents are not limited to these compound examples. Although the reaction solvent used in the oxidation reaction depends upon the type of the compound to be synthesized, the solvent need not be used, or any solvent may be used as long as it does not inhibit the effect of the oxidizing agent and does not react with the oxidizing agent. Although the reaction temperature also depends upon the type of the compound to be synthesized, the reaction temperature of −70° C. to 100° C. usually produces good results in some cases, and the reaction temperature is preferably −30° C. to 80° C.

In an example of a method for synthesizing a compound having the structure represented by formula (1) having an oxetanyl terminal group, a compound having a structure represented by formula (13) in which the terminal group in the structure represented by formula (1) is a mercapto group is mixed with 3-halogeno(alkyl)oxetane, and a metal alkoxide is added to the resultant mixture to produce good results in some cases.

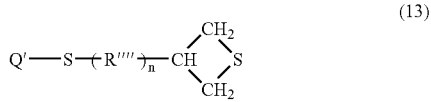

(13)

(wherein Q' represents a hydrogen atom or a straight, branched or cyclic alkyl group having 1 to 10 carbon atoms and at least a mercapto group or its thia derivative, an aryl group, or an aralkyl group, R'''' represents a substituted or unsubstituted straight, branched or cyclic hydrocarbon group having 1 to 6 carbon atoms, and n represents an integer of 0 to 3.)

Also, an alkali metal salt or metal alkoxide may be reacted with a compound having the structure represented by formula (13) to form a salt, and then the salt is reacted with 3-halogeno(alkyl)oxetane to produce good results in some cases. Although the reaction solvent used in the reaction depends upon the type of the compound to be synthesized, the solvent need not be used, or any solvent may be used as long as it does not inhibit the reaction of the alkali metal salt or metal alkoxide, the compound having the structure represented by formula (13) and the halogenated hydrocarbon compound, and does not react with the alkali metal salt or metal alkoxide. Although the reaction temperature also depends upon the type of the compound to be synthesized, the reaction temperature of −70° C. to 50° C. usually produces good results in some cases, and the reaction temperature is preferably −50° C. to 50° C.

As the 3-halogeno(alkyl)oxetane compound used in this method, any known 3-halogeno(alkyl)oxetane compound or a 3-halogeno(alkyl)oxetane compound obtained by halogenating a 3-hydroxy(alkyl)oxetane compound may be used. Preferred examples of the oxetane compound include 3-chloro(alkyl)oxetane compounds such as 3-chloromethyloxetane, 3-chloroethyloxetane, and the like; 3-chloro(alkyl)-3-(alkyl)oxetane compounds such as 3-chloromethyl-3-methyloxetane, 3-chloromethyl-3-ethyloxetane, 3-chloroethyl-3-ethyloxetane, and the like. However, the oxetane compounds are not limited to these examples.

Preferred examples of the compound having the structure represented by formula (13) include aliphatic compounds such as 3-(mercaptomethylthio)thietane, 3-(mercaptoethylthio)thietane, 3-(1-mercaptopropyl-2-thio)thietane, 3-(1-mercaptopropyl-3-thio)thietane, 3-(2-mercaptopropyl-2-thio)thietane, 3-(1-mercaptobutyl-4-thio)thietane, 3-(mercaptomethylthiomethylthio)thietane, 3-(mercaptoethylthioethylthio)thietane, 3-(2-mercapto-1-hydroxypropyl-3-thio)thietane, 3-(3-mercapto-2-hydroxypropyl-1-thio)thietane, 3-(2-mercaptomethylthiophene-5-methylthio)thietane, 3-(2-mercaptomethyl-1,4-dithiane-5-methylthio)thietane, 3-(1-mercaptocyclohexane-2-thio)thietane, 3-(1-mercaptocyclohexane-3-thio)thietane, 3-(1-mercaptocyclohexane-4-thio)thietane, and the like; aromatic compounds such as 3-(1-mercaptobenzene-2-thio)thietane, 3-(1-mercaptobenzene-3-thio)thietane, 3-(1-mercaptobenzene-4-thio)thietane, 3-(1-mercaptomethylbenzene-2-methylthio)thietane, 3-(1-mercaptomethylbenzene-3-methylthio)thietane, 3-(1-mercaptomethylbenzene-4-methylthio)thietane, and the like. However, the compounds are not limited to these examples.

In an example of a method for synthesizing a compound having the structure represented by formula (1) having an epoxy and/or episulfido terminal group, 3-mercapto(alkyl)thietane is reacted with epihalohydrin in the presence of an alkali catalyst to synthesize (3-chloro-2-hydroxypropanylthio) (alkyl)thietane as a halohydrin compound, and then the halohydrin compound is dehydrochlorinated with an alkali to obtain 3-(2,3-epoxypropylthio)(alkyl)thietane. As the alkali used, either an inorganic alkali or organic alkali may be used, and an alkali metal or alkali earth metal hydroxide, an alkali metal or alkali earth metal carbonate, an alkali metal or alkali earth metal bicarbonate, ammonia, a tertiary amine, a secondary amine, a primary amine, a metal alkoxide, or the like is preferably used. Although the solvent used for adding the alkali depends upon the type of the compound to be synthesized, the solvent need not be used, or any solvent may be used as long as it does not inhibit the reaction with the alkali and does not react with the alkali. Although the reaction temperature also depends upon the type of the compound to be synthesized, the reaction temperature of −30° C. to 100° C. usually produces good results in some cases. The reaction temperature is preferably −10° C. to 80° C., and more preferably 10° C. to 60° C. In another method, a 3-hydroxy(alkyl)thietane compound is condensed with 1-chloro-3-mercaptopropane-2-ol in the presence of an acid catalyst to synthesize (3-chloro-2-hydroxypropylthio) (alkyl)thietane as a halohydrin compound, and then the halohydrin compound is dehydrochlorinated with an alkali in the same manner as described above. Although the solvent used for condensation depends upon the type of a compound to be synthesized, the solvent need not be used, or any solvent may be used as long as it does not inhibit the condensation, and a solvent which permits azeotropic dehydration is preferably used for increasing the reaction efficiency. Although the reaction temperature also depends upon the type of the compound to be synthesized, the reaction temperature of 0° C. to 120° C. usually produces good results in some cases, and the reaction temperature is preferably 20° C. to 110° C., and more preferably 30° C. to 90° C.

Preferred examples of the resultant 3-(2,3-epoxypropylthio) (alkyl)thietane compound include aliphatic compounds such as 3-(2,3-epoxypropylthio)thietane, 3-(2,3-epoxypropyldithio)thietane, 3-(2,3-epoxypropylthiomethyl)thietane, 3-(2,3-epoxypropylthioethylthio)thietane, 3-(2,3-epoxypropylthiopropylthio)thietane, 3-(2,3-epoxypropylthiobutylthio)thietane, 3-(2,3-epoxypropylthiomethylthiometylthio)thietane, 3-(2,3-epoxypropylthioethylthioethylthio)thietane, 3-(2,3-epoxypropylthiohydroxypropylthio)thietane, 3-[2-(2,3-epoxypropylthio)methylthiophene-5-methylthio]thietane, 3-[2-(2,3-epoxypropylthio)methyl-1,4-dithiane-5-methylthio]thietane, 3-[1-(2,3-epoxypropylthio)cyclohexane-2-thia]thietane, 3-[1-(2,3-epoxypropylthio)cyclohexane-3-thia]thietane, 3-[1-(2,3-epoxypropylthio)cyclohexane-4-thia]thietane, and the like; aromatic compounds such as 3-[1-(2,3-epoxypropylthio)benzene-2-thia]thietane, 3-[1-(2,3-epoxypropylthio)benzene-3-thia]thietane, 3-[1-(2,3-epoxypropylthio)benzene-4-thia]thietane, 3-[1-(2,3-epoxypropylthio)methylbenzene-2-methylthio]thietane, 3-[1-(2,3-epoxypropylthio)methylbenzene-3-methylthio]thietane, 3-[1-(2,3-epoxypropylthio)methylbenzene-4-methylthio]thietane, and the like. However, the thietane compounds are not limited to these examples.

The resultant compound having the structure represented by formula (1) having an epoxy terminal group may be reacted with a thianation agent to synthesize a compound having a structure represented by formula (1) having an episulfido terminal group. As the thianation agent, a thiocyanate, thiourea, triphenylphosphine sulfide, or the like, preferably, a thiocyanate or thiourea, is used. The compound may be synthesized by a reaction, if required, in a catalytic amount of at least one polar solvent selected from organic acids such as formic acid, acetic acid, propionic acid, phthalic acid, and the like, halogenated products anhydrides thereof, inorganic acids such as hydrochloric acid, sulfuric acid, nitric acid, phosphoric acid, and the like, water, alcohols, ketones, ethers, and esters, and if required, a known organic solvent which can dissolve the resultant episulfide compound are used for obtaining the episulfide compound. The reaction may be effected in at least one polar solvent in an amount substantially equivalent to thiourea to form an isothiuronium salt, the polar solvent being selected from organic acids such as formic acid, acetic acid, propionic acid, phthalic acid, and the like, halogenated products and anhydrides of these organic acids, inorganic acids such as hydrochloric acid, sulfuric acid, nitric acid, phosphoric acid, and the like, water, alcohols, ketones, ethers, and esters. Then, the same alkali as described above may be added to a solution containing the isothiuronium salt or the isolated isothiuronium salt and reacted with the isothiuronium salt to synthesize the episulfide compound. Preferred examples of the alkali include ammonia, sodium hydroxide, potassium hydroxide, calcium hydroxide, sodium carbonate, potassium carbonate, and ammonium carbonate, and aqueous solutions of these alkalis. Although the solvent used for adding the alkali depends upon the type of a compound to be synthesized, the solvent need not be used, or any solvent may be used as long as it does not inhibit the reaction with the alkali and does not react with the alkali. Although the reaction temperature also depends upon the type of the compound to be synthesized, the reaction temperature of −30° C. to 100° C. usually produces good results in some cases, and the reaction temperature is preferably −10° C. to 80° C., and more preferably 10° C. to 60° C.

Preferred examples of the thietane compound having the structure represented by formula (1) in which the terminal group is an episulfide group include aliphatic compounds such as 3-(2,3-epithiopropylthio)thietane, 3-(2,3-epithiopropyldithio)thietane, 3-(2,3-epithiopropylthiomethyl)thietane, 3-(2,3-epithiopropylthioethylthio)thietane, 3-(2,3-epithiopropylthiopropylthio)thietane, 3-(2,3-epithiopropylthiobutylthio)thietane, 3-(2,3-epithiopropylthiomethylthiomethylthio)thietane, 3-(2,3-epithiopropylthioethylthioethylthio)thietane, 3-(2,3-epithiopropylthiohydroxypropylthio)thietane, 3-[2-(2,3-epithiopropylthio)methylthiophene-5-methylthio]thietane, 3-[2-(2,3-epithiopropylthio)methyl-1,4-dithiane-5-methylthio]thietane, 3-[1-(2,3-epithiopropylthio)cyclohexane-2-thio]thietane, 3-[1-(2,3-epithiopropylthio)cyclohexane-3-thio]thietane, 3-[1-(2,3-epithiopropylthio)cyclohexane-4-thio]thietane, and the like; aromatic compounds such as 3-[1-(2,3-epithiopropylthio)benzene-2-thia]thietane, 3-[1-(2,3-epithiopropylthio)benzene-3-thia]thietane, 3-[1-(2,3-epithiopropylthio)benzene-4-thia]thietane, 3-[1-(2,3-epithiopropylthio)methylbenzene-2-methylthio]thietane, 3-[1-(2,3-epithiopropylthio)methylbenzene-3-methylthio]thietane, 3-[1-(2,3-epithiopropylthio)methylbenzene-4-methylthio]thietane, and the like. However, the thietane compounds are not limited to these examples.

A method for synthesizing a compound having the structure represented by formula (1) in which the terminal group is an amino group, an isocyanato group, an isothiocyanato (meth)acryl group, an allyl group, a vinyl group, or an isopropenyl group is the following general method.

A compound having an amino group is synthesized by a known alkyl halide amination method for aminating a thietane compound having a halogeno terminal group. For example, an alkali metal azide compound is reacted with an alkyl halide to synthesize an azide compound, and then the azide compound is converted to an amino compound by a Bechamp reduction process, a process using lithium aluminum hydride or sodium boron hydride and iodine, or a process using hydrogen in the presence of an Adams catalyst. The amino compound can also be synthesized by an ammonolysis process, a Gabriel's process, a Delepine process, a hexamine process, or the like in some cases. Also, the target compound can easily be synthesized by reacting the thietane compound having a hydroxyl group and/or mercapto group at the terminal with halogenoalkylamine (or its salt such as hydrochloride or the like) in the presence of an alkali.

A compound having an isocyanato group can be synthesized by reacting the amino compound with phosgene. The reaction with phosgene is effected by a cold-hot two-step method comprising reacting an amine with phosgene at a low temperature and then reacting the reaction product with phosgene at a high temperature, a hydrochloride method comprising forming a hydrochloride using an amine and hydrochloric acid gas, and then the hydrochloride with phosgene, or the like. The compound can also be synthesized by reacting a halogenated acid ester such as chloroacetate ester or the like with the thietane compound having a hydroxyl group and/or mercapto group at the terminal to form a hydrazide compound using hydrazine, and then reacting the hydrazide compound with nitrous acid to produce a Curtius rearrangement reaction through an acid azide compound.

A compound having an isothiocyanato group can be synthesized by a method in which the amino compound is reacted with carbon disulfide and an alkali such as caustic soda or the like, and then the reaction product is decomposed with a chlorinating agent such as alkyl chloroformate or the like. Also, a method of reacting thiophosgene with the amino compound is preferably used.

A compound having a (meth)acryl group is synthesized by a method in which a halogenated acid halide such as chloropropionyl chloride or the like is reacted with the thietane compound having a hydroxyl group and/or mercapto group at the terminal, and then the reaction product is dehydrohalogenated with an alkali such as a tertiary amine or alkali metal salt or its aqueous solution, a metal alkoxide, or the like, or a method in which the thietane compound is reacted directly with an acid chloride such as (meth)acrylic chloride or the like.

A compound having an ally group, a vinyl group, or an isopropenyl group is synthesized by a method in which the thietane compound having a hydroxy group and/or mercapto group at the terminal is reacted with an ally halide such as allyl chloride or the like, a vinyl halide such as vinyl bromide or the like, or isopropenyl halide such as isopropenyl chloride or the like in the presence of the alkali. The methods for synthesizing the compounds having the structures represented by formula (1) having an amino terminal group, an isocyanato terminal group, an isothiocyanato terminal group, a (meth)acryl terminal group, an allyl terminal group, a vinyl terminal group, and an isopropenyl terminal group, respectively, depends upon the structures of the target compounds and are not limited to the above-described methods. The used solvent and reaction temperature also depend upon the target compounds and are not limited. Preferred examples of these compounds having the structures represented by formula (1) having an amino terminal group, an isocyanato terminal group, a (meth)acryl terminal group, an allyl terminal group, a vinyl terminal group, and an isopropenyl terminal group, respectively, include 3-(aminomethylthio)thietane, 3-[iso(thio)cyanatothio]thietane, 3-(aminoethylthio)thietane, 3-[iso(thio)cyanatoethylthio]thietane, 3-[(meth)acryloylthio]thietane, 3-(allylthio)thietane, 3-(vinylthio)thietane, 3-(isopropenylthio)thietane, and the like. The compounds are not limited to these examples.

Besides the above-described 3-thietanyl compounds, 2-thietanyl compounds can be synthesized in the same manner as the 3-thietanyl compounds. More specifically, 3,3-dimercapto-1-halogenopropane is reacted with 3,3-dialkyloxy-1-halogenoproane (for example, 3-chloropropionaldehyde diethylacetal) and hydrogen sulfide. The resultant 3,3-dimercapto-1-halogenoproane is reacted with the same alkali as described above in the presence or absence of a solvent to synthesize 2-mercaptoethietane through intramolecular cyclization. The thus-obtained 2-mercaotpthietane can be subjected to the above-described various reactions to synthesize compounds having various structures derived from a 2-thietanyl group.

A polymerizable composition containing the sulfur-containing cyclic ompound having the structure represented by formula (1) of the present invention comprises at least one sulfur-containing cyclic compound having the structure represented by formula (1). However, in some cases, in order to obtain a good resin, a method or operation generally used for synthesizing an organic compound, such as purification, cleaning, hot insulation, cold insulation, filtration, reduced-pressure treatment, or the like is preferably performed, or a known compound is preferably added as a stabilizer or resin modifier for improving a resin and handleability, for example, for controlling the optical physical properties such as the refractive index and Abbe's number, and the like, physical properties such as a hue, light resistance, weather resistance, heat resistance, impact resistance, hardness, specific gravity, linear expansion coefficient, polymerization shrinkability, water absorption, hygroscopicity, chemical resistance, viscoelasticity, and the like, and transmittance and transparency of a resin produced by curing the polymerizable composition, and controlling the viscosity of the polymerizable composition, and preservation and transport handleability. Examples of compounds added for improving stability such as long-term preservation stability, polymerization stability and thermal stability include a polymerization retardant, a polymerization inhibitor, a deoxidant, an antioxidant, and the like. However, the compounds are not limited to these examples.

Purification of the polymerizable composition is a means for improving the transparency of the resin produced by curing, or increasing the purity of the resin to improving the hue thereof. As a method for purifying the polymerizable composition containing the sulfur-containing cyclic compound having the structure represented by formula (1) of the present invention, any known method, for example, distillation, recrystallization, column chromatography (a silica gel method, an activated carbon method, an ion-exchange resin method, or the like), extraction, or the like, may be performed with any timing as long as the transparency and hue of the resin obtained by curing the purified composition are improved.

As a method for cleaning the polymerizable composition, a method for improving the transparency and hue of the resin obtained by curing may be used with timing when or after the synthesized polymerizable composition is taken out. In this method, the composition is washed with a polar and/or nonpolar solvent to remove or reduce a resin transparency inhibitor, for example, an inorganic salt used for synthesizing the polymerizable composition or secondarily produced in synthesizing the composition, such as an ammonium salt, thiourea, or the like. Although the solvent used depends upon the polymerizable composition to be cleaned and the polarity of a solution containing the polymerizable composition, and is not limited, a solvent which can dissolve a component to be removed, and which is incompatible with the polymerizable composition to be cleaned and the solution containing the polymerizable composition is preferably used. The solvent may be used singly, or a mixture of at least two solvents may be used. Although the amount of a component to be removed depends upon the purpose and application, the amount is preferably as low as possible. The amount is preferably 5000 ppm or less, more preferably 1000 ppm or less, and most preferably 100 ppm or less.

As a hot insulation, cold insulation or filtration method for the polymerizable composition, a method for improving the transparency and hue of the resin obtained by curing is generally used with timing when or after the synthesized polymerizable composition is taken out. In the hot insulation method, for example, when the polymerizable composition is crystallized to deteriorate handleability during storage, the polymerizable composition is melted by heating within a range causing no deterioration in the performance of the polymerizable composition and the resin obtained by curing the polymerizable composition. Although the heating temperature range and heat melting method depend upon the compound constituting the polymerizable composition to be handled and are not limited, the heating temperature is generally in a range of the solidification point+50° C., and preferably the solidification point+20° C. In this method, the composition may be melted by mechanically stirring with a stirring device or bubbling with an inert gas for moving an internal liquid. The cold insulation method is generally performed for improving the preservation stability of the polymerizable composition. However, when the composition has a high melting point and thus has a problem about handleability after crystallization, consideration must be given to the storage temperature. Although the cold insulation temperature depends upon the structure and preservation stability of the compound constituting the polymerizable composition to be handled and is not limited, the polymerizable composition containing a compound having the structure represented by formula (1) is preferably stored at a low temperature of 20° C. or less, and more preferably 10° C. or less. However, when the composition has a high melting point, storage at a temperature higher than the solidification temperature generally improves handleability in some cases of use. When heat-melting can easily be performed, storage at a temperature lower than the solidification temperature has no problem.

The polymerizable composition used for optical applications is required to have high transparency, and thus the polymerizable composition is preferably filtered with a filter having a small pore size. Although the pore size of the filter used is usually 0.05 to 10 µm, the pore size is preferably 0.05 to 5 µm, and more preferably 0.1 to 5 µm, from the viewpoint of operationality and performance. In many cases, filtration of the polymerizable composition containing the sulfur-containing cyclic compound of the present invention produces good results without exception. Although a low filtration temperature near the solidification temperature produces more desirable results in some cases, filtration is preferably performed at a temperature causing no trouble in the filtration work when solidification proceeds during filtration.

The reduced-pressure treatment is a means for removing a solvent, dissolved gas and odor which deteriorate the performance of the resin generally produced by curing the polymerizable composition. Since a dissolved solvent generally decreases the refractive index of the resultant resin and deteriorates the heat resistance thereof, the dissolved solvent must be removed as much as possible. Although the allowable amount of the dissolved solvent depends upon the structure of the compound constituting the polymerizable composition to be handled and the structure of the dissolved solvent and is not limited, the allowable amount is usually 1% or less, and preferably 5000 ppm or less. The dissolved gas inhibits polymerization or causes the problem of mixing bubbles in the resultant resin, and is thus preferably removed. Particularly, a moisture gas such as water vapor or the like is preferably removed by bubbling with a dry gas. The amount of the dissolved gas depends upon the structure of the compound constituting the polymerizable composition, the physical properties, structure and type of the dissolved gas and is not limited.

Examples of the resin modifier include known thietane compounds other than the thietane compound contained in the polymerizable composition of the present invention, dithietane compounds, trithietane compounds, thiolane compounds, dithiolane compounds, trithiolane compounds, dithiane compounds, trithiane compounds, episulfide compounds, epoxy compounds, amine compounds, thiol compounds, hydroxyl compounds including phenol compounds, iso(thio)cyanato compounds, mercapto organic acids, organic acids, anhydrides, amino acids, mercapto amines, olefins including (meth)acrylates, cyclic organic and inorganic compounds each having a sulfur atom or selenium atom, and the like. Of these resin modifiers, epoxy compounds, iso(thio)cyanato compounds, olefins including (meth)acrylates are preferred for overcoming brittleness of the resultant resin and for improving the impact resistance thereof. Also, amine compounds, thiol compounds, and phenol compounds are preferred for improving the hue of the resultant resin. Particularly, a compound having at least one SH group and/or a NH group and/or a $NH_2$ group is more preferred.

Examples of an episulfide compound used as the resin modifier in the present invention include epithioethyl compounds such as bis(1,2-epithioethyl) sulfide, bis(1,2-epithioethyl) disulfide, bis(epithioethylthio)methane, bis(epithioethylthio)benzene, bis[4-(epithioethylthio)phenyl] sulfide, bis[4-(epithioethylthio)phenyl]methane, and the like; chain aliphatic 2,3-epithiopropylthio compounds such as bis(2,3-epithiopropyl) sulfide, bis(2,3-epithiopropyl) disulfide, bis (2,3-epithiopropylthio)methane, 1,2-bis(2,3-epithiopropylthio)ethane, 1,2-bis(2,3-epithiopropylthio)propane, 1,3-bis (2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis (2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis (2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[[2-(2,3-epithiopropylthio)ethyl] thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, 1,11-bis(2,3-epithiopropylthio)-5,7-bis(2,3-epithiopropylthiomethyl)-3,6,9-trithiaundecane, and the like; alicyclic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[[2-(2,3-epithiopropylthio)ethyl]thiomethyl]-1,4-dithiane, 2,5-bis(2,3-epithiopropylthiomethyl)-2,5-dimethyl-1,4-dithiane, and the like; aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl] sulfide, bis[4-(2,3-epithiopropylthio)phenyl] sulfone, 4,4'-bis(2,3-epithiopropylthio)biphenyl, and the like; monofunctional episulfide compounds such as ethylene sulfide, propylene sulfide, mercaptopropylene sulfide, mercaptobutene sulfide, epithiochlorohydrin, and the like; chain aliphatic 2,3-epithiopropyloxy compounds such as bis(2,3-epithiopropyl) ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methylpropane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methylpentane, 1,5-bis(2,3-epithiopropyloxy)-3-thiapentane, 1,6-bis(2,3-epithiopropyloxy)hexane, 1,6-bis(2,3-epithiopropyloxy)-2-methylhexane, 3,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl) propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis(2,3-epithiopropyloxymethyl)-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl)-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl)-3,6-dithiaoctane, 1,8-bis(2,3-epithiopropyloxy)-4,4-bis(2,3-epithiopropyloxymethyl)-3,6-dithiaoctane, 1,8-bis(2,3-epithiopropyloxy)-2,5-bis(2,3-epithiopropyloxymethyl)-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epithiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, 1,11-bis(2,3-epithiopropyloxy)-5,7-bis(2,3-epithiopropyloxymethyl)-3,6,9-trithiaundecane, and the like; alicyclic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, 2,5-bis(2,3-epithiopropyloxymethyl)-2,5-dimethyl-1,4-dithiane, and the like; aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2-bis(2,3-epithiopropyloxymethyl)benzene, 1,3-bis(2,3-epithiopropyloxymethyl)benzene, 1,4-bis(2,3-epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl] sulfide, bis[4-(2,3-epithiopropyloxy)phenyl] sulfone, 4,4'-bis(2,3-epithiopropyloxy)biphenyl, and the like. However, the episulfide compounds are not limited to these examples.

Of these compound examples, bis(1,2-epithioethyl) sulfide, bis(1,2-epithioethyl) disulfide, bis(2,3-epithiopropyl) disulfide, bis(2,3-epithiopropylthio)methane and bis(2,3-epithiopropyl) disulfide are preferred, and bis(1,2-epithioethyl) sulfide, bis(1,2-epithioethyl) disulfide, and bis(2,3-epithiopropyl) disulfide are more preferred.

Examples of an epoxy compound used as the resin modifier in the present invention include phenolic epoxy compounds each obtained by a condensation reaction of an epihalohydrin compound and a polyhydric phenol compound such as bisphenol A glycidyl ether or the like, alcoholic epoxy compounds each obtained by condensation of an epihalohydrin compound and a polyhydric alcohol compound such as hydrogenated bisphenol A glycidyl ether or the like, glycidyl ester-type epoxy compounds each obtained by condensation of an epihalohydrin compound and a polyvalent organic acid compound such as 3,4-epoxycyclohexylmethyl-3',4'-epoxycyclohexane carboxylate, diglycidyl 1,2-hexahydrophthalate, or the like, amine-type epoxy compounds each obtained by condensation of a secondary amine compound and an epihalohydrin compound, aliphatic polyvalent epoxy compounds such as vinylcyclohexene diepoxide, and the like.

Examples of sulfide group-containing epoxide compounds and ether group-containing epoxide compounds include chain aliphatic 2,3-epoxypropylthio compounds such as bis(2,3-epoxypropyl) sulfide, bis(2,3-epoxypropyl) disulfide, bis(2,3-epoxypropylthio)methane, 1,2-bis(2,3-epoxypropylthio)ethane, 1,2-bis(2,3-epoxypropylthio)propane, 1,3-bis(2,3-epoxypropylthio)propane, 1,3-bis(2,3-epoxypropylthio)-2-methylpropane, 1,4-bis(2,3-epoxypropylthio)butane, 1,4-bis(2,3-epoxypropylthio)-2-methylbutane, 1,3-bis(2,3-epoxypropylthio)butane, 1,5-bis(2,3-epoxypropylthio)pentane, 1,5-bis(2,3-epoxypropylthio)-2-methylpentane, 1,5-bis(2,3-epoxypropylthio)-3-thiapentane, 1,6-bis(2,3-epoxypropylthio)hexane, 1,6-bis(2,3-epoxypropylthio)-2-methylhexane, 3,8-bis(2,3-epoxypropylthio)-3,6-dithiaoctane, 1,2,3-tris(2,3-epoxypropylthio)propane, 2,2-bis(2,3-epoxypropylthio)-1,3-bis(2,3-epoxypropylthiomethyl)propane, 2,2-bis(2,3-epoxypropylthiomethyl)-1-(2,3-epoxypropylthio)butane, 1,5-bis(2,3-epoxypropylthio)-2-(2,3-epoxypropylthiomethyl)-3-thiapentane, 1,5-bis(2,3-epoxypropylthio)-2,4-bis(2,3-epoxypropylthiomethyl)-3-thiapentane, 1-(2,3-epoxypropylthio)-2,2-bis(2,3-epoxypropylthiomethyl)-4-thiahexane, 1,5,6-tris(2,3-epoxypropylthio)-4-(2,3-epoxypropylthiomethyl)-3-thiahexane, 1,8-bis(2,3-epoxypropylthio)-4-(2,3-epoxypropylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2,3-epoxypropylthio)-2,4,5-tris(2,3-epoxypropylthiomethyl)-3,6-dithiaoctane, 1,1,1-tris[[2-(2,3-epoxypropylthio)ethyl]

thiomethyl]-2-(2,3-epoxypropylthio)ethane, 1,1,2,2-tetrakis[[2-(2,3-epoxypropylthio)ethyl]thiomethyl]ethane, 1,11-bis(2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, 1,11-bis(2,3-epoxypropylthio)-5,7-bis(2,3-epoxypropylthiomethyl)-3,6,9-trithiaundecane, and the like; alicyclic 2,3-epoxypropylthio compounds such as 1,3-bis(2,3-epoxypropylthio)cyclohexane, 1,4-bis(2,3-epoxypropylthio)cyclohexane, 1,3-bis(2,3-epoxypropylthiomethyl)cyclohexane, 1,4-bis(2,3-epoxypropylthiomethyl)cyclohexane, 2,5-bis(2,3-epoxypropylthiomethyl)-1,4-dithiane, 2,5-bis[[2-(2,3-epoxypropylthio)ethyl]thiomethyl]-1,4-dithiane, 2,5-bis(2,3-epoxypropylthiomethyl)-2,5-dimethyl-1,4-dithiane, and the like; aromatic 2,3-epoxypropylthio compounds such as 1,2-bis(2,3-epoxypropylthio)benzene, 1,3-bis(2,3-epoxypropylthio)benzene, 1,4-bis(2,3-epoxypropylthio)benzene, 1,2-bis(2,3-epoxypropylthiomethyl)benzene, 1,3-bis(2,3-epoxypropylthiomethyl)benzene, 1,4-bis(2,3-epoxypropylthiomethyl)benzene, bis[4-(2,3-epoxypropylthio)phenyl]methane, 2,2,-bis[4-(2,3-epoxypropylthio)phenyl]propane, bis[4-(2,3-epoxypropylthio)phenyl] sulfide, bis[4-(2,3-epoxypropylthio)phenyl] sulfone, 4,4'-bis(2,3-epoxypropylthio)biphenyl, and the like; monofunctional epoxy compounds such as ethylene oxide, propylene oxide, glycidol, epichlorohydrin, and the like; chain aliphatic 2,3-epoxypropyloxy compounds such as bis(2,3-epoxypropyl)ether, bis(2,3-epoxypropyloxy)methane, 1,2-bis(2,3-epoxypropyloxy)ethane, 1,2-bis(2,3-epoxypropyloxy)propane, 1,3-bis(2,3-epoxypropyloxy)propane, 1,3-bis(2,3-epoxypropyloxy)-2-methylpropane, 1,4-bis(2,3-epoxypropyloxy)butane, 1,4-bis(2,3-epoxypropyloxy)-2-methylbutane, 1,3-bis(2,3-epoxypropyloxy)butane, 1,5-bis(2,3-epoxypropyloxy)pentane, 1,5-bis(2,3-epoxypropyloxy)-2-methylpentane, 1,5-bis(2,3-epoxypropyloxy)-3-thiapentane, 1,6-bis(2,3-epoxypropyloxy)hexane, 1,6-bis(2,3-epoxypropyloxy)-2-methylhexane, 3,8-bis(2,3-epoxypropyloxy)-3,6-dithiaoctane, 1,2,3-tris(2,3-epoxypropyloxy)propane, 2,2-bis(2,3-epoxypropyloxy)-1,3-bis(2,3-epoxypropyloxymethyl)propane, 2,2,-bis(2,3-epoxypropyloxymethyl)-1-(2,3-epoxypropyloxy)butane, 1,5-bis(2,3-epoxypropyloxy)-2-(2,3-epoxypropyloxymethyl)-3-thiapentane, 1,5-bis(2,3-epoxypropyloxy)-2,4-bis(2,3-epoxypropyloxymethyl)-3-thiapentane, 1-(2,3-epoxypropyloxy)-2,2-bis(2,3-epoxypropyloxymethyl)-4-thiahexane, 1,5,6-tris(2,3-epoxypropyloxy)-4-(2,3-epoxypropyloxymethyl)-3-thiahexane, 1,8-bis(2,3-epoxypropyloxy)-4-(2,3-epoxypropyloxymethyl)-3,6-dithiaoctane, 1,8-bis(2,3-epoxypropyloxy)-4,5-bis(2,3-epoxypropyloxymethyl)-3,6-dithiaoctane, 1,8-bis(2,3-epoxypropyloxy)-4,4-bis(2,3-epoxypropyloxymethyl)-3,6-dithiaoctane, 1,8-bis(2,3-epoxypropyloxy)-2,5-bis(2,3-epoxypropyloxymethyl)-3,6-dithiaoctane, 1,8-bis(2,3-epoxypropyloxy)-2,4,5-tris(2,3-epoxypropyloxymethyl)-3,6-dithiaoctane, 1,1,1-tris[[2-(2,3-epoxypropyloxy)ethyl]thiomethyl]-2-(2,3-epoxypropyloxy)ethane, 1,1,2,2-tetrakis[[2-(2,3-epoxypropyloxy)ethyl]thiomethyl]ethane, 1,11-bis(2,3-epoxypropyloxy)-4,8-bis(2,3-epoxypropyloxymethyl)-3,6,9-trithiaundecane, 1,11-bis(2,3-epoxypropyloxy)-4,7-bis(2,3-epoxypropyloxymethyl)-3,6,9-trithiaundecane, 1,11-bis(2,3-epoxypropyloxy)-5,7-bis(2,3-epoxypropyloxymethyl)-3,6,9-trithiaundecane, and the like; alicyclic 2,3-epoxypropyloxy compounds such as 1,3-bis(2,3-epoxypropyloxy)cyclohexane, 1,4-bis(2,3-epoxypropyloxy)cyclohexane, 1,3-bis(2,3-epoxypropyloxymethyl)cyclohexane, 1,4-bis(2,3-epoxypropyloxymethyl)cyclohexane, 2,5-bis(2,3-epoxypropyloxymethyl)-1,4-dithiane, 2,5-bis[[2-(2,3-epoxypropyloxy)ethyl]thiomethyl]-1,4-dithiane, 2,5-bis(2,3-epoxypropyloxymethyl)-2,5-dimethyl-1,4-dithiane, and the like; aromatic 2,3-epoxypropyloxy compounds such as 1,2-bis(2,3-epoxypropyloxy)benzene, 1,3-bis(2,3-epoxypropyloxy)benzene, 1,4-bis(2,3-epoxypropyloxy)benzene, 1,2-bis(2,3-epoxypropyloxymethyl)benzene, 1,3-bis(2,3-epoxypropyloxymethyl)benzene, 1,4-bis(2,3-epoxypropyloxymethyl)benzene, bis[4-(2,3-epoxypropyloxy)phenyl]methane, 2,2-bis[4-(2,3-epoxypropyloxy)phenyl]propane, bis[4-(2,3-epoxypropyloxy)phenyl] sulfide, bis[4-(2,3-epoxypropyloxy)phenyl] sulfone, 4,4'-bis(2,3-epoxypropyloxy)biphenyl, and the like. However, the epoxide compounds are not limited to these examples.

Examples of an amine compound which can be added as the resin modifier include monofunctional primary amine compounds such as ethylamine, n-propylamine, isopropylamine, n-butylamine, sec-butylamine, tert-butylamine, pentylamine, hexylamine, heptylamine, octylamine, decylamine, laurylamine, myristylamine, 3-pentylamine, 2-ethylhexylamine, 1,2-dimethylhexylamine, allylamine, aminomethylbicycloheptane, cyclopentylamine, cyclohexylamine, 2,3-dimethylcyclohexylamine, aminomethylcyclohexane, aniline, benzylamine, phenethylamine, 2,3- or 4-methylbenzylamine, o-, m- or p-methylaniline, o-, m- or p-ethylaniline, aminomorpholine, naphthylamine, furfurylamine, α-aminodiphenylmethane, toluidine, aminopyridine, aminophenol, aminoethanol, 1-aminopropanol, 2-aminopropanol, aminobutanol, aminopentanol, aminohexanol, methoxyethylamine, 2-(2-aminoethoxy)ethanol, 3-ethoxypropylamine, 3-propoxypropylamine, 3-butoxypropylamine, 3-isopropoxypropylamine, 3-isobutoxypropylamine, 2,2-diethoxyethylamine, and the like; primary polyamine compounds such as ethylenediamine, 1,2- or 1,3-diaminopropane, 1,2-, 1,3- or 1,4-diaminobutane, 1,5-diaminopentane, 1,6-diaminohexane, 1,7-diaminoheptane, 1,8-diaminooctane, 1,10-diaminodecane, 1,2-, 1,3- or 1,4-diaminocyclohexane, o-, m- or p-diaminobenzene, 3,4- or 4,4'-diaminobenzophenone, 3,4- or 4,4'-diaminodiphenyl ether, 4,4'-diaminodiphenylmethane, 4,4'-diaminodiphenyl sulfide, 3,3'- or 4,4'-diaminodiphenyl sulfone, 2,7-diaminofluorene, 1,5-, 1,8- or 2,3-diaminonaphthalene, 2,3-, 2,6- or 3,4-diaminopyridine, 2,4- or 2,6-diaminotoluene, m- or p-xylylenediamine, isophoronediamine, iaminomethylbicycloheptane, 1,3- or 1,4-diaminomethylcyclohexane, 2- or 4-aminopiperidine, 2- or 4-aminomethylpiperidine, 2- or 4-aminoethylpiperidine, N-aminoethylmorpholine, N-aminopropylmorpholine, and the like; monofunctional secondary amine compounds such as diethylamine, dipropylamine, di-n-butylamine, di-sec-butylamine, diisobutylamine, di-n-pentylamine, di-3-pentylamine, dihexylamine, dioctylamine, di(2-ethylhexyl)amine, methylhexylamine, diallylamine, N-methylallylamine, piperidine, pyrrolidine, diphenylamine, N-methylamine, N-ethylamine, dibenzylamine, N-methylbenzylamine, N-ethylbenzylamine, dicyclohexylamine, N-methylaniline, N-ethylaniline, dinaphthylamine, 1-methylpiperazine, morpholine, and the like; secondary polyamine compounds such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'- diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,5-diaminopentane, N,N'-diethyl-1,6-diaminohexane, N,N'-diethyl-1,7-diaminoheptane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di-(4-pieridyl)butane, tetramethylguanidine, and the like. However, the amine compounds are not limited to these examples. The amine compounds may be used singly or in a mixture of at least two compounds. Of these compound examples, benzylamine and piperazines are more preferred compounds.

A thiol compound which can be added as the resin modifier may contain at least one sulfur atom other than a mercapto group. Examples of a monofunctional thiol compound include aliphatic mercaptan compounds such as methyl mercaptan, ethyl mercaptan, propyl mercaptan, butyl mercaptan, octyl mercaptan, dodecyl mercaptan, tert-dodecyl mercaptan, hexadecyl mercaptan, octadecyl mercaptan, cyclohexyl mercaptan, benzyl mercaptan, ethylphenyl mercaptan, 2-mercaptomethyl-1,3-dithiolane, 2-mercaptomethyl-1,4-dithiane, and the like; aromatic mercaptan compounds such as thiophenol, mercaptotoluene, and the like. Examples of a di- or higher-functional polythiol compounds include aliphatic polythiol compounds such as 1,1-methanedithiol, 1,2-ethanedithiol, 1,1-propanedithiol, 1,2-propanedithiol, 1,3-propanedithiol, 2,2-propanedithiol, 1,6-hexanedithiol, 1,2,3-propantrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, thiomalic acid bis(2-mercaptoethyl ester), 2,3-dimercapto-1-propanol (2-mercaptoacetate), 2,3-dimercapto-1-propanol (3-mercaptoprionate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl) ether, ethylene glycol bis(2-mercaptoacetate), ethylene glycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate), tetrakis(mercaptomethyl)methane, and the like; aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 2,5-toluenedithiol, 3,4-toluenedithiol, 1,3-di(p-methoxyphenyl)propane-2,2-dithiol, 1,3-diphenylpropane-2,2-dithiol, phenylmethane-1,1-dithiol, 2,4-di(p-mercaptophenyl)pentane, and the like; polythiols each having a heterocycle, such as 2-methylamino-4,6-dithiol-sym-triazine, and the like; aromatic polytiol compounds each having a sulfur atom other than a mercapto group, such as 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, and the like, nuclear alkylated products thereof; aliphatic polythiol compounds each having a sulfur group other than a mercapto group, such as bis(mercaptomethyl) sulfide, bis(mercaptoethyl) sulfide, bis(mercaptopropyl) sulfide, bis(mercaptomethylthio) methane, bis(2-mercaptoethylthio)methane, bis(3-mercaptopropylthio)methane, 1,2-bis(mercaptomethylthio)ethane, 1,2-bis(2-mercaptoethylthio)ethane, 1,2-bis(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, 1,2-bis[(2-mercaptoethyl)thio]-3-mercaptopropane, 4,8-dimercaptomethyl-1,11-mercapto-3,6,9-trithiaundecane, 4,7-dimercaptomethyl-1,11-mercapto-3,6,9-trithiaundecane, 5,7-dimercaptomethyl-1,11-mercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, 1,1,2,2-tetrakis(mercaptomethylthio)ethane, 1,1,3,3-tetrakis(mercaptomethylthio)propane, bis(2,3-dimercaptopropyl) sulfide, bis(1,3-dimercaptopropyl) sulfide, 2,5-dimercapto-1,4-dithiane, 2,5-dimercaptomethyl-1,4-dithiane, 2,5-dimercaptomethyl-2,5-dimethyl-1,4-dithiane, 4,6-bis(mercaptomethylthio)-1,3-dithiane, bis(mercaptomethyl) disulfide, bis(mercaptoethyl) disulfide, bis(mercaptopropyl) disulfide, and the like, thioglycolic acid and mercaptopropionic acid esters of these polytiol compounds, hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptoprionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thiodiglycolic acid bis(2-mercaptoethyl ester), thiodipropionic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), dithioglycolic acid bis(2,3-dimercaptopropyl ester), dithiodipropionic acid bis(2,3-dimercaptopropyl ester), and the like; heterocyclic compounds each having a sulfur atom other than a mercapto group, such as 3,4-thiophenedithiol, 2,5-dimercapto-1,3,4-thiadiazole, Bismuthiol, and the like.

Examples of a mercapto compound having a hydroxyl group include 2-mercaptoethanol, 3-mercapto-1,2-propanediol, glycerin di(mercaptoacetate), 1-hydroxy-4-mercaptocyclohexane, 2,4-dimercaptophenol, 2-mercaptohydroquinone, 4-mercaptophenol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), dipentaerythritol pentakis(3-mercaptopropionate), hydroxymethyl-tris(mercaptoethylthiomethyl)methane, 1-hydroxyethylthio-3-mercaptoethylthiobenzene, and the like. However, the thiol compounds are not limited to these examples. Also, halogenated products of these polythiol compounds, such as chlorinated and brominated products, may be used. These compounds may be used singly or in a mixture of at least two compounds. Of these thiol compounds, polysulfide-type polythiol compounds are preferred from the viewpoint of the refractive index of the resultant resin. Polythiol compounds composed of only carbon, hydrogen and sulfur atoms are more preferred. In consideration of the heat resistance of the resulting resin, the compounds are more preferably di- or higher-functional rather than monofunctional, and most preferably tetra- or higher-functional. Preferred examples of these compounds include bis(mercaptomethyl) sulfide, 1,1,2,2-tetrakis(mercaptomethylthio)ethane, 1,1,3,3-tetrakis(mercaptomethylthio)propane, 4,8-dimercaptomethyl-1,11-mercapto-3,6,9-trithiaundecane, 4,7-dimercaptomethyl-1,11-mercapto-3,6,9-trithiaundecane, 5,7-dimercaptomethyl-1,11-mercapto-3,6,9-trithiaundecane, and the like.

Examples of hydroxy compounds including phenol compounds used as the resin modifier in the present invention are mono- or higher-functional mono or polyol compounds including compounds having phenolic hydroxyl groups. The hydroxy compounds also include compounds each having a sulfur atom in its molecule. Examples of monofunctional compounds include aliphatic monofunctional alcohol compounds such as methanol, ethanol, n-propanol, isopropanol, n-butanol, sec-butanol, tert-butanol, pentanol, isoamyl alcohol, hexanol, heptanol, octanol, nonyl alcohol, decanol, dodecyl alcohol, cetyl alcohol, isotridecyl alcohol, stearyl alcohol, 2-ethyl-1-hexanol, ally alcohol, methoxyethanol, ethoxyethanol, phenoxyethanol, cyclopropanol, cyclobutanol, cyclopentanol, cyclohexanol, cyclooctanol, benzyl alcohol, phenylethyl alcohol, methylcyclohexanol, furfuryl alcohol, tetrahydrofurfuryl alcohol, methyl lactate, ethyl lactate, butyl lactate, and the like; aromatic monofuctional phenol compounds such as phenol, cresol, ethylphenol, methoxyphenol, ethoxyphenol, methoxyethylphenol, cumylphenol, phenoxyphenol, tert-butylphenol, naphthol, and the like.

Examples of di- or higher-functional polyol compounds include polyols such as ethylene glycol, diethylene glycol, propylene glycol, dipropylene glycol, butylene glycol, neopentyl glycol, glycerin, trimethylolethane, trimethylolpropane, butanetriol, 1,2-methyl glycoside, pentaerythritol, dipentaerythritol, tripentaerythritol, sorbitol, erythritol, threitol, mannitol, ribitol, arabinitol, xylitiol, allitol, dorsitol, glycol, inositol, hexane triol, triglycerol, triethylene glycol, polyethylene glycol, tris(2-hydroxyethyl) isocyanurate, cyclobutanediol, cyclopentanediol, cyclohexanediol, cycloheptanediol, cyclooctanediol, cyclohexanedimethaol, hydroxypropylcyclohexanol, bicyclo[4,3,0]-nonanediol, dicylcohexanediol, tricyclo[5,3,1,1]dodecanediol, bicyclo[4,3,0]-nonanedimethanol, dicylcohexanediol, tricyclo[5,3,1,1]dodecanediethanol, spiro[3,4]octanediol, butylcyclohexanediol, 1,1-bicyclohexylidenediol, cyclohexanetriol, maltitol, lactitol, dihydroxynaphthalene, trihydroxynaphthalene, tetrahydroxynaphthalene, dihydroxybenzene, benzenetriol, biphenyltetraol, trihydroxyphenanthrene, bisphenol A, bisphenol F, xylylene glycol, bis(2-hydroxyethoxy)benzene, bisphenol A-bis(2-hydroxyethyl ether), tetrabromobisphenol A, tetrabromobisphenol A-bis(2-hydroxyethyl ether), dibromoneopentyl glycol, and the like; condensation reaction products of these polyols with organic polybasic acids such as oxalic acid, glutamic acid, adipic acid, acetic acid, propionic acid, phthalic acid, isophthalic acid, salicylic acid, pyromellitic acid, 3-bromopropionic acid, 2-bromoglycolic acid, dicarboxycyclohexane, butanetetracarboxylic acid, bromophthalic acid, and the like; addition reaction products of the polyols with alkylene oxides such as ethylene oxide, propylene oxide, and the like. However, the polyol compounds are not limited to these examples. Furthermore, halogenated products of these polyols, such as chlorinated products, brominated products, and the like, may be used.

Examples of mono or polyol compounds each having a sulfur atom include bis[4-(hydroxyethoxy)phenyl] sulfide, bis[4-(2-hydroxypropoxy)phenyl] sulfide, bis[4-(2,3-dihydroxypropoxy)phenyl] sulfide, bis[4-(4-hydroxycyclohexyloxy)phenyl] sulfide, and bis[2-methyl-4-(hydroxyethoxy)-6-butylphenyl] sulfide, and compounds having an average of 3 or less molecules of ethylene oxide and/or propylene oxide per hydroxyl group, which are added to these mono or polyol compounds, bis(2-hydroxyethyl) sulfide, 1,2-bis(2-hydroxyethylmercapto)ethane, bis(2-hydroxyethyl) disulfide, 1,4-dithiane-2,5-diol, bis(2,3-dihydroxypropyl) sulfide, tetrakis(4-hydroxy-2-thiabutyl)methane, bis(4-hydroxyphenyl) sulfone (bisphenol S), tetrabromobisphenol S, tetramethylbisphenol S, 4,4-thiobis(6-tert-butyl-3-methylphenol), 1,3-bis(2-hydroxyethylthioethyl)cyclohexane, and the like. However, the polyol compounds are not limited to these examples. Furthermore, halogenated products of these compounds, such as chlorinated products and brominated products, may be used.

Examples of an iso(thio)cyanate compound used as the resin modifier in the present invention include monofunctional isocyanate compounds such as methyl isocyanate, ethyl isocyanate, n-propyl isocyanate, isopropyl isocyanate, n-butyl isocyanate, sec-butyl isocyanate, tert-butyl isocyanate, pentyl isocyanate, hexyl isocyanate, heptyl isocyanate, octyl isocyanate, decyl isocyanate, lauryl isocyanate, myristyl isocyanate, octadecyl isocyanate, 3-pentyl isocyanate, 2-ethylhexyl isocyanate, 2,3-dimethylcyclohexyl isocyanate, 2-methoxyphenyl isocyanate, 4-methoxyphenyl isocyanate, α-methylbenzyl isocyanate, phenylethyl isocyanate, phenyl isocyanate, o-, m- or p-tolyl isocyanate, cyclohexyl isocyanate, benzyl isocyanate, isocyanatomethylbicycloheptane, and the like; aliphatic polyisocyanate compounds such as hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl) carbonate, bis(isocyanatoethyl) ether, lisine diisocyanatomethyl ester, lisine triisocyanate, xylylene diisocyanate, bis(isocyanatoethyl)benzene, bis(isocyanatopropyl)benzene, α, α, α', α'-tetramethylxylylene diisocyanate, bis(isocyanatobutyl) benzene, bis(isocyanatomethyl)naphthalene, bis(isocyanatomethyl)diphenyl ether, bis(isocyanatoethyl) phthalate, mesitylene triisocyanate, 2,6-di(isocyanatomethyl)furan, and the like; alicyclic polyisocyanate compounds such as isophorone diisocyanate, bis(isocyanatomethyl)cyclohexane, dicyclohexylmethane diisocyanate, cyclohexane diisocyanate, methylcyclohexane diisocyanate, dicyclohexyldimethylmethane diisocyanate, 2,2-dimethyldicyclohexylmethane diisocyanate, 2,5-bis (isocyanatomethyl) bicyclo-[2,2,1]-heptane, 2,6-bis (isocyanatomethyl) bicyclo-[2,2,1]-heptane, 3,8-bis (isocyanatomethyl) tricyclodecane, 3,9-bis (isocyanatomethyl) tricyclodecane, 4,8-bis(isocyanatomethyl) tricyclodecane, 4,9-bis(isocyanatomethyl) tricyclodecane, and the like; aromatic polyisocyanate compounds such as phenylene diisocyanate, tolylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4-diphenylmethane diisocyanate, 3,3-dimethyldiphenylmethane-4,4-diisocyanate, bibenzyl-4,4-diisocyanate, bis(isocyanatophenyl)ethylene, 3,3-dimethoxybiphenyl-4,4-diisocyanate, phenylisocyanatoethyl isocyanate, hexahydrobenzene diisocyanate, hexahydrodiphenylmethane-4,4-diisocyanate, and the like; sulfur-containing aliphatic isocyanate compounds such as bis(isocyanatomethyl) sulfide, bis(isocyanatoethyl) sulfide, bis(isocyanatopropyl) sulfide, bis(isocyanatohexyl) sulfide, bis(isocyanatomethyl) sulfone, bis(isocyanatomethyl) disulfide, bis(isocyanatoethyl) disulfide, bis(isocyanatopropyl) disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane, and the like; aromatic sulfide-type isocyanate compounds such as diphenylsulfido-2,4-diisocyanate, diphenylsulfido-4,4-diisocyanate, 3,3-dimethoxy-4,4-diisocyanatodibenzyl thioether, bis(4-isocyanatomethylbenzene) sulfide, 4,4-methoxybenzene thioethylene glycol-3,3-diisocyanate, and the like; aromatic disulfide-type isocyanate compounds such as diphenyl disulfido-4,4-diisocyanate, 2,2-dimethyldiphenyl disulfide-5,5-diisocyanate, 3,3-dimethyldiphenyl disulfido-5,5-diisocyanate, 3,3-dimethyldiphenyl disulfido-6,6-diisocyanate, 4,4-dimethyldiphenyl disulfido-5,5-diisocyanate, 3,3-dimethoxydiphenyl disulfido-4,4-diisocyanate, 4,4-dimethoxydiphenyl disulfido-3,3-diisocyanate, and the like; sulfur-containing heterocyclic compounds such as 2,5-diisocyanatothiophene, 2,5-bis(isocyanatomethyl)thiophene, and the like.

Other examples include 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, 4,5-bis(isocyanatomethyl)-2-methyl-1,3-dithiolane, and the like. However, the isocyanate compounds are not limited to these examples. Also, halogenated products such as chlorinated products and brominated products, alkylated products, alkoxylated products, nitro-substituted products, prepolymer-type modified products with polyhydric alcohols, carbodiimide-modified products, urea-modified products, burette-modified products, dimerization or trimerization reaction products of these compounds may be used.

Examples of isothiocyanate compounds include monofunctional isothiocyanate compounds such as methyl isothiocyanate, ethyl isothiocyanate, n-propyl isothiocyanate, isopropyl isothiocyanate, n-butyl isothiocyanate, sec-butyl isothiocyanate, tert-butyl isothiocyanate, pentyl isothiocyanate, hexyl isothiocyanate, heptyl isothiocyanate, octyl isothiocyanate, decyl isothiocyanate, lauryl isothiocyanate, myristyl isothiocyanate, octadecyl isothiocyanate, 3-pentyl isothiocyanate, 2-ethylhexyl isothiocyanate, 2,3-dimethylcyclohexyl isothiocyanate, 2-methoxyphenyl isothiocyanate, 4-methoxyphenyl isothiocyanate, α-methylbenzyl isothiocyanate, phenylethyl isothiocyanate, phenyl isothiocyanate, o-, m- or p-tolyl isothiocyanate, cyclohexyl isothiocyanate, benzyl isothiocyanate, isothiocyanatomethylbicycloheptane, and the like; aliphatic polyisothiocyanate compounds such as 1,6-diisothiocyanatohexane, p-phenyleneisopropylidene diisothiocyanate, and the like; alicyclic polyisothiocyanate compounds such as cyclohexane diisothiocyanate, diisothiocyanatomethylbicycloheptane, and the like; aromatic isothiocyanate compounds such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4-diisothiocyanato-1,1-biphenyl, 1,1-methylene bis(4-isothiocyanatobenzene), 1,1-methylene bis(4-isothiocyanato-2-methylbenzene), 1,1-methylene bis(4-isothiocyanato-3-methylbenzene), 1,1-(1,2-ethanediyl) bis (isothiocyanatobenzene), 4,4-diisothiocyanatobenzophenone, 4,4-diisothiocyanato-3,3-dimethylbenzophenone, diphenyl ether-4,4-diisothiocyanate, diphenylamine-4,4-diisothiocyanate, and the like; carbonyl isothiocyanate compounds such as 1,3-benzenedicarbonyl diisothiocyanate, 1,4-benzenedicarbonyl diisothiocyanate, (2,2-pyridine)-4,4-dicarbonyl diisothiocyanate, and the like. However, the isothiocyanate compounds are not limited to these examples.

Examples of an isothiocyanate compound having one or more sulfur atoms other than an isothiocyanato group include sulfur-containing aliphatic isothiocyanate compounds such as thiobis(3-isothiocyanatopropane), thiobis(2-isothiocyanatoethane), dithiobis(2-isothiocyanatoethane), and the like; sulfur-containing aromatic isothiocyanate compounds such as 1-isothiocyanato-4-[(2-isothiocyanato)sulfonyl]benzene, thiobis(4-isothiocyanatobenzene), sulfonyl bis (4-isothiocyanatobenzene), dithiobis(4-isothiocyanatobenzene), and the like; sulfur-containing heterocyclic compounds such as 2,5-diisothiocyanatothiophene, 2,5-diisothiocyanato-1,4-dithiane, and the like. However, the sulfur-containing isothiocyanate compounds are not limited to these examples. Also, halogenated products such as chlorinated products and brominated products, alkylated products, alkoxylated products, nitro-substituted products, prepolymer-type modified products with polyhydric alcohols, carbodiimide-modified products, urea-modified products, burette-modified products, dimerization or trimerization reaction products of these compounds may be used.

Examples of an isothiocyanate compound having an isocyanato group include aliphatic and alicyclic compounds such as 1-isocyanato-6-isothiocyanatohexane, 1-isocyanato-4-isothiocyanatocyclohexane, and the like; aromatic compounds such as 1-isocyanato-4-isothiocyanatobenzene, 4-methyl-3-isocyanato-1-isothiocyanatobenzene, and the like; heterocyclic compounds such as 2-isocyanato-4,6-diisothiocyanato-1,3,5-triazine, and the like; and compounds each having a sulfur atom other than an isothiocyanato group, such as 4-isocyanato-4'-isothiocyanatodiphenyl sulfide, 2-isocyanato-2'-isothiocyanatodiethyl disulfide, and the like. However, the isothiocyanate compounds each having an isocyanato groups are not limited to these examples. Also, halogenated products such as chlorinated products and brominated products, alkylated products, alkoxylated products, nitro-substituted products, prepolymer-type modified products with polyhydric alcohols, carbodiimide-modified products, urea-modified products, burette-modified products, dimerization or trimerization reaction products of these compounds may be used.

Preferred examples of a mercapto organic acid compound used as the resin modifier in the present invention include thioglycolic acid, 3-mercaptopropionic acid, thioacetic acid, thiolactic acid, thiomalic acid, thiosalicylic acid, and the like. However, the mercapto organic acids are not limited to these examples. Also, the mercapto organic acid compounds may be used singly or in a mixture of at least two compounds.

Preferred examples of organic acids and anhydrides thereof include monofunctional organic acids such as hydrocarbon organic acids, such as formic acid, acetic acid, propionic acid, butyric acid, benzoic acid, p-toluenesulfonic acid, methanesulfonic acid, and the like, and halogen-, nitro- and cyano-substituted products thereof; acid anhydrides such as trifluoroacetic anhydride, chloroacetic anhydride, dichloroacetic anhydride, trichloroacetic anhydride, phthalic anhydride, hexahydrophthalic anhydride, methylhexahydrophthalic anhydride, methyltetrahydrophthalic anhydride, methylnorbornene acid anhydride, methylnorbornane acid anhydride, maleic anhydride, trimellitic anhydride, pyromellitic anhydride, and the like; difunctional organic acids such as phthalic acid, succinic acid, and the like; sulfur-containing organic acids such as thiodiglycolic acid, thiodipropionic acid, dithiodipropionic acid, and the like. However, the organic acids are not limited to these examples.

Preferred examples of olefins include (meth)acrylate compounds such as benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethyelne glycol dimethacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, dimethyloltricyclodecane diacrylate, trimethylolpropane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methyl thioacrylate, methyl thiomethacrylate, phenyl thioacrylate, benzyl thiomethacrylate, xylyleneditiol diacrylate, xylyleneditiol dimethacrylate, mercaptoethyl sulfide diacrylate, mercaptoethyl sulfide dimethacrylate, and the like; ally compounds such as ally diglycidyl ether, dially phthalate, dially terephthalate, dially isophthalate, dially carbonate, diethylene glycol bisally carbonate, and the like; vinyl compounds such as styrene, chlorostyrene, methylstyrene, bromostyrene, dibromostyrene, divinylbenzene, 3,9-divinyl spirobi(m-dioxane), divinyl sulfide, divinyl disulfide, and the like; diisopropenylbenzene; and the like. However, the olefins are not limited to these examples.

Furthermore, the above-described several types of resin modifiers may be used singly or in a mixture of at least two types. Although the amount of the resin modifiers added depends upon the structure of a compound constituting the polymerizable composition and is not limited, the amount is usually in the range of 0.001 wt % to 50 wt % based on the amount of the polymerizable composition. The adding amount is preferably 0.005 wt % to 25 wt %, and more preferably 0.01 wt % to 15 wt %.

The polymerizable composition containing the sulfur-containing cyclic compound having the structure represented by formula (1) of the present invention can be cured by a known method for polymerizing a sulfur-containing cyclic compound. The type and amount of the curing catalyst used for obtaining a cured resin, and the type and ratio of the monomer used depend upon the structure of a compound constituting the polymerizable composition and are not limited. However, as the type of the curing catalyst, amines other than the resin modifier used in the present invention, phosphines, organic acids and salts, esters, anhydrides thereof, inorganic acids, quaternary ammonium salts, quaternary phosphonium salts, tertiary sulfonium salts, secondary iodonium salts, Lewis acids, radical polymerization catalysts, cationic polymerization catalysts, and the like are conventionally used.

Examples of the curing catalyst include aliphatic and aromatic tertiary amines such as triethylamine, tri-n-butylamine, tri-n-hexylamine, N,N-diisopropylethylamine, triethylenediamine, triphenylamine, N,N-dimethylethanolamine, N,N-diethylethanolamine, N,N-dibutylethanolamine, triethanolamine, N-ethyldiethanolamine, N,N-dimethylbenzylamine, N,N-diethylbenzylamine, tribenzylamine, N-methyldibenzylamine, N,N-dimethylcyclohexylamine, N,N-diethylcyclohexylamine, N,N-dimethylbutylamine, N-methyldicyclohexylamine, N-methylmorpholine, N-isopropylmorpholine, pyridine, quinoline, N,N-dimethylaniline, N,N-diethylaniline, α-, β- or γ-picoline, 2,2'-bipyridyl, 1,4-dimethylpiperazine, dicyandiamide, tetramethylethylenediamine, hexamethylenetetramine, 1,8-diazabicyclo(5,4,0)-7-undecene, 2,4,6-tris(N,N-dimethylaminomethyl)phenol, and the like; phosphines such as trimethylphosphine, triethylphosphine, tri-n-propylphosphine, triisopropylphosphine, tri-n-butylphosphine, triphenylphosphine, tribenzylphosphine, 1,2-bis(diphenylphosphino)ethane, 1,2-bis(dimethylphosphino)ethane, and the like; trihalogenoacetic acids and esters, anhydrides and salts thereof, such as trifluoroacetic acid, trichloroacetic acid, trifluoroacetic anhydride, ethyl trifluoroacetate, sodium trifluoroacetate, and the like; p-toluenesulfonic acid; methanesulfonic acid; trihalogenomethanesulfonic acids and esters, anhydrides and salts thereof, such as trifluoromethanesulfonic acid, trifluoromethanesulfonic anhydride, ethyl trifluoromethanesulfonate, sodium trifluoromethanesulfonate, and the like; inorganic acids such as hydrochloric acid, sulfuric acid, nitric acid, and the like; quaternary ammonium salts such as tetramethylammonium chloride, tetrabutylammonium chloride, tetrabutylammonium bromide, and the like; quaternary phosphonium salts such as tetramethylphosphonium chloride, tetrabutylphosphonium chloride, tetrabutylphosphonium bromide, and the like; tertiary sulfonium salts, such as trimethylsulfonium bromide, tributylsulfonium bromide, and the like; secondary iodonium salts such as diphenyliodonium bromide, and the like; Lewis acids such as dimethyltin dichloride, dibutyltin dichloride, dibutyltin dilaurate, dibutyltin diacetate, tetrachlorotin, dibutyltin oxide, diacetoxytetrabutyldistannoxane, zinc chloride, acetylacetone zinc, aluminum chloride, aluminum fluoride, triphenyl aluminum, acetylacetone aluminum, isopropoxide aluminum, tetrachlorotitanium and complexes thereof, tetraiodotitanium, titanium alkoxides such as dichlorotitanium diisopropoxide, titanium isopropoxide, and the like, calcium acetate, boron trihalide compounds such as boron trifluoride, boron trifluoride diethyl ether complex, boron trifluoride piperidine complex, boron trifluoride ethyleneamine complex, boron trifluoride acetic acid complex, boron trifluoride phosphoric acid complex, boron trifluoride t-butyl methyl ether complex, boron trifluoride dibutyl ether complex, boron trifluoride THF complex, boron trifluoride methyl sulfide complex, boron trifluoride phenol complex, and the like, boron trichloride complexes, and the like; radial polymerization catalysts such as 2,2'-azobis(2-cyclopropylpropionitrile), 2,2'-azobis(4-methoxy-2,4-dimethylvaleronitrile), 2,2'-azobis(2,4-dimethylvaleronitrile), t-butylperoxy-2-ethylhexanoate, n-butyl-4,4'-bis(t-butylperoxy)valerate, t-butylperoxybenzoate, and the like; cationic polymerization catalysts such as diphenyliodonium hexafluorophosphate, diphenyliodonium hexafluoroarsenate, diphenyliodonium hexafluoroantimony, triphenylsulfonium tetrafluoroborate, triphenylsulfonium hexafluorophosphate, triphenylsulfonium hexafluoroarsenate, (tolylcumyl)iodonium tetrakis(pentafluorophenyl)borate, and the like. However, the curing catalysts are not limited to these examples.

The above-described curing catalysts may be used singly or in a mixture of at least two compounds. A mixture of at least two types of curing catalysts having different reactivities is preferably used for improving the monomer handleability, and the optical physical properties, hue, transparency, and optical strain (stria) of the resultant resin in some cases.

Of the above compounds, preferred examples include organotin compounds such as dimethyltin dichloride, dibutyltin dichloride, dibutyltin dilaurate, dibutyltin diacetate, tetrachlorotin, dibutyltin oxide, diacetoxytetrabutylstannoxane, and the like; trihalogenoacetic acids and esters, anhydrides and salts thereof, such as trifluoroacetic acid, trichloroacetic acid, trifluoroacetic anhydride, ethyl trifluoroacetate, sodium trifluoroacetate, and the like; p-toluenesulfonic acid; methanesulfonic acid; trihalogenomethanesulfonic acids and esters, anhydrides and salts thereof, such as trifluoromethanesulfonic acid, trifluoromethanesulfonic anhydride, ethyl trifluoromethanesulfonate, sodium trifluoromethanesulfonate, and the like; Lewis acids such as boron trihalides and complexes thereof, such as boron trifluoride; boron trifluoride complexes such as boron trifluoride diethyl ether complex, boron trifluoride piperidine complex, boron trifluoride ethylamine complex, boron trifluoride acetic acid complex, boron trifluoride phosphoric acid complex, boron trifluoride t-butyl methyl ether complex, boron trifluoride dibutyl ether complex, boron trifluoride THF complex, boron trifluoride methyl sulfide complex, boron trifluoride phenol complex, and the like, boron trichloride and complexes thereof, and the like; cationic polymerization catalysts such as diphenyliodonium hexafluorophosphate, diphenyliodonium hexafluoroarsenate, diphenyliodonium hexafluoroantimony, triphenylsulfonium tetrafluoroborate, triphenylsulfonium hexafluorophosphate, triphenylsulfonium hexafluoroarsenate (tolylcumyl) iodonium tetrakis(pentafluorophenyl)borate, and the like. Of these compounds, dimethyltin dichloride, trifluoromethanesulfonic acid and anhydrides, esters, and salts thereof, and boron trifluoride complexes are more preferred.

The amount of the curing catalyst added is in the range of 0.001 wt % to 10 wt %, preferably 0.01 wt % to 5 wt %, and more preferably 0.005 wt % to 1 wt %, based on the total weight of the polymerizable composition. With the amount of curing catalyst added in this range, a sufficiently cured resin can be produced, and a pot life can be maintained. Also, the obtained resin has good transparency and optical physical properties in some cases. The curing catalyst may be added directly to any of the above-described compounds of the present invention, or may be dissolved or dispersed in another compound and then added. In some cases, the curing catalyst is preferably dissolved or dispersed in another compound and then added, for obtaining good results. Furthermore, the curing catalyst is preferably added in a nitrogen atmosphere or a dry gas atmosphere for obtaining good results in some cases. In order to improve the performance of the resultant resin, the amount of the unreactive groups remaining in the resin is preferably 0.5 wt % or less, and more preferably 0.3 wt % or less, based on the total weight of the resin.

In curing and molding the polymerizable composition containing the sulfur-containing cyclic compound having the structure represented by formula (1) of the present invention, a known molding method may be used according to purposes, and various additives other than the above-described additives, such as a stabilizer, a resin modifier, a chain extender, a crosslinking agent, a HALS-type photostabilizer or the like, a benzotriazole ultraviolet absorber or the like, a hindered phenol antioxidant or the like, a coloring inhibitor, an anthraquinone disperse dye or the like, a filler, a silicone-type external mold releasing agent or acidic phosphate or quaternary ammonium salt internal mold releasing agent, an adhesion improving agent, and the like may be used. Although the amount of each of the additives which can be added depends upon the type, structure and effect of each additive and is not limited, the adding amount is usually in the range of 0.001 wt % to 10 wt %, and preferably 0.01 to 5 wt %, based on the total weight of the polymerizable composition. The amount of the dye added is preferably in the range of 1 ppb to 100 ppm, not in the above-described range. Within these ranges, a sufficiently cured resin can be produced, and the obtained resin has good transparency and optical physical properties in some cases.

A typical polymerization method for producing a resin (for example, a plastic lens) by curing the composition of the present invention is a casting polymerization. Namely, the polymerizable composition of the present invention is injected into a mold which is maintained by a gasket, a tape, or the like. Although the injection operation may be performed in a normal atmosphere unless there is a problem, it is preferably performed in a nitrogen atmosphere or dry gas atmosphere for producing good results in some cases. The inside of the mold may be previously replaced with a nitrogen gas or dry gas. The polymerizable composition may be mixed with the curing catalyst and resin modifier, and subjected to an operation such as a reduced-pressure treatment under 10 kPa or less, such as degassing, filtration, or the like according to demand. Next, the composition can be cured by heating in a heating apparatus such as an oven, water, or the like, and then taken out.

The polymerization method, polymerization conditions, and the like for producing the resin by curing the composition of the present invention depend upon the type and amount of the curing catalyst used, and the type and ratio of the monomer used, and are not limited.

The heating polymerization conditions for the polymerizable composition injected into the mold according to the present invention depend upon the composition and structure of the polymerizable composition containing a compound having the structure represented by formula (1) of the present invention, and are not limited. Also, the conditions greatly depend upon the type of the resin modifier used, the type of the curing catalyst used, the shape of the mold, etc., and are not limited. However, the polymerization temperature is about −50° C. to 200° C., preferably −20° C. to 150° C., and more preferably in the temperature range of 0° C. to 130° C. The polymerization time is 0.01 to 100 hours, preferably 0.05 to 50 hours, and more preferably 0.1 to 25 hours. In some cases, the polymerization conditions can be programmed with a low temperature, a temperature rise, a temperature drop, and the like.

The polymerization time of the composition of the present invention can be reduced by irradiation with an energy beam such as an electron beam, an ultraviolet ray, or the like. In this case, the curing catalyst such as the radical polymerization catalyst, the cationic polymerization catalyst, or the like may be added. Also, the cured resin may be subjected to a treatment such as annealing or the like. Although the annealing condition depends upon the structure of the compound constituting the polymerizable composition to be cured, and the structure of the resultant resin and is not limited, annealing is usually performed at 30° C. to 200° C., preferably 50° C. to 150° C., and more preferably 70° C. to 130° C.

Furthermore, the resin of the present invention can be molded into various shapes by using various molds for casting polymerization, so that the resin can be used for various applications of a resin required to have a high refractive index and transparency, such as eyeglasses, a camera lens, a light emitting diode (LED), and the like. Particularly, the resin is preferably used as an optical material for eyeglasses and a camera lens, and the like.

Furthermore, a lens using the optical material of the present invention can be subjected to a physical or chemical treatment such as surface polishing, an antistatic treatment, a hard coating treatment, a non-reflecting coating treatment, a dyeing treatment, or the like, for preventing reflection, imparting high hardness, a defogging property or fashion property, or improving abrasion resistance or chemical resistance according to demand.

Although the present invention will be described in detail below with reference to examples, the present invention is not limited to these examples. The thermal stability of the obtained polymerizable composition was. tested by measuring a change in purity of a main component in a heat retention test at 40° C. in a nitrogen atmosphere. One month after, when the purity was decreased by 10% or more, the stability was evaluated as x(not good), and when the purity was decreased by 10% or less, the stability was evaluated as ○ (good). Of the performance tests of the resultant cured resin, the optical physical properties, specific gravity, optical strain, and impact resistance were evaluated by the following test methods.

Refractive index (ne) and Abbe's number (ve); measured with a Pulfrich's refractometer at 20° C.

Specific gravity: Measured by an Archimedes method at 20° C.

Optical strain: Visually observed under a high-pressure mercury lamp.

Impact resistance: A iron ball of 16 g was dropped on a lens (−3D) having a central thickness of about 1.0 mm from a height of 127 cm, and a damage state of the lens was observed. A damaged lens was evaluated as × (not good), and an undamaged lens was evaluated as ○ (good)

EXAMPLE 1

190 g of thiourea, 253 g of 35% hydrochloric acid, and 250 g of water were charged in a reactor provided with a stirrer and thermometer, and then 156 g of 3-thietanol was added dropwisely to the resultant mixture under stirring. The mixture was further stirred at 30° C. for 24 hours for aging. Then, 177 g of 24% ammonia water was added dropwisely to the mixture maintained at 30° C., and then stirred at 30° C. for 15 hours for aging. After still standing, 134 g of a lower layer was removed as an organic layer. The thus-removed lower layer was simply distilled under reduced pressure to recover a distillate of 40° C. under 106 Pa. As a result, 69 g of distillate was obtained, and the distillate was 3-mercaptothietane (referred to as "compound A" hereinafter).

The identification data of compound A is shown below.

TABLE 1

| Elemental Analysis | | C | H | S |
|---|---|---|---|---|
| | Theoretical value | 33.9% | 5.7% | 60.4% |
| | Analytical value | 34.2% | 5.1% | 60.7% |
| MS spectrum (EI method) | $M^+ = 106$ | | | |
| IR spectrum | 642 cm$^{-1}$; sulfide 2539 cm$^{-1}$; mercaptan | | | |
| $^1$H-NMR spectrum (CDCL$_3$) | a; 2.1 ppm (1H) b; 3.4 ppm (4H) c; 4.3 ppm (1H) | | | |
| $^{13}$C-NMR spectrum (CDCL$_3$) | 1; 37.6 ppm 2; 39.3 ppm | | | |

$$\begin{array}{c} \phantom{S}\overset{b,2}{CH_2} \\ S\diagup\phantom{xx}\diagdown \\ \phantom{Sxx}CH-\overset{a}{SH} \\ \diagdown\phantom{xx}\diagup \\ \phantom{Sx}\underset{1,c}{CH_2} \end{array} \quad (A)$$

EXAMPLE 2

163 g of 3-chlorothietane (referred to as "compound B" hereinafter) and 200 g of toluene were charged in a reactor provided with a stirrer and thermometer, and then a sodium sulfide aqueous solution obtained by reacting 60 g of 70% sodium hydrosulfide, 60 g of water and 62 g of 49% caustic soda was added dropwisely to the resultant mixture under stirring at 5° C. After aging for 2 hours, the resultant toluene layer was washed with acetic acid and a salt aqueous solution, dehydrated with magnesium sulfate, and then concentrated to obtain 135 g of concentration residue. The thus-obtained residue was purified by silica gel chromatography using hexane and chloroform as developing solvents. As a result of analysis, 84 g of bis(3-thietanyl) sulfide (referred to as "compound C" hereinafter) was obtained. The stability of the thus-obtain compound C was evaluated as ○ (good).

The identification data of compound C is shown below.

TABLE 2

| Elemental Analysis | | C | H | S |
|---|---|---|---|---|
| | Theoretical value | 40.5% | 5.6% | 53.9% |
| | Analytical value | 41.6% | 5.2% | 53.2% |
| MS spectrum (EI method) | $M^+ = 178$ | | | |
| IR spectrum | 653 cm$^{-1}$; sulfide | | | |
| $^1$H-NMR spectrum (CDCL$_3$) | a; 3.2 ppm (4H) b; 3.5 ppm (4H) c; 4.2 ppm (2H) | | | |
| $^{13}$C-NMR spectrum (CDCL$_3$) | 1; 34.5 ppm 2; 43.5 ppm | | | |

TABLE 2-continued

| Elemental Analysis | C | H | S |
|---|---|---|---|

$$\underset{CH_2}{\overset{CH_2}{S}}\!\!>\!\!\underset{c,2}{\overset{a,b,1}{CH}}\!-\!S\!-\!\underset{CH_2}{\overset{CH_2}{CH}}\!\!<\!\!\underset{CH_2}{\overset{}{S}} \quad (C)$$

EXAMPLE 3

159 g of compound A and 20 g of toluene were charged in a reactor provided with a stirrer and thermometer, and then 890 g of 12.7% sodium hypochlorite aqueous solution was added dropwisely to the resultant mixture under stirring at 10° C. After aging at 10° C. for 2 hours, the resultant toluene layer was washed twice with a salt aqueous solution, dehydrated with magnesium sulfate, filtered, and then concentrated to obtain 148 g of concentration residue. The thus-obtained residue was purified by silica gel chromatography using hexane and chloroform as developing solvents. As a result of analysis, the residue was bis(3-thietanyl) disulfide (referred to as "compound D" hereinafter). The stability of the thus-obtain compound D was evaluated as ○ (good).

The identification data of compound D is shown below.

TABLE 3

| Elemental analysis | | C | H | S |
|---|---|---|---|---|
| | Theoretical value | 34.2% | 4.8% | 61.0% |
| | Analytical value | 34.8% | 5.1% | 60.1% |
| MS spectrum (EI method) | $M^+$ = 210 | | | |
| IR spectrum | 650 $cm^{-1}$; sulfide | | | |
| $^1$H-NMR spectrum (CDCL$_3$) | a; 3.2 ppm (4H) b; 3.5 ppm (4H) c; 4.5 ppm (2H) | | | |
| $^{13}$C-NMR spectrum (CDCL$_3$) | 1; 33.2 ppm 2; 47.5 ppm | | | |

$$\underset{CH_2}{\overset{CH_2}{S}}\!\!>\!\!\underset{c,2}{\overset{a,b,1}{CH}}\!-\!SS\!-\!\underset{CH_2}{\overset{CH_2}{CH}}\!\!<\!\!\underset{}{\overset{}{S}} \quad (D)$$

EXAMPLE 4

159 g of compound A was charged in a reactor provided with a stirrer and thermometer, and then 300 g of 27% sodium methoxide was added dropwisely to the compound under stirring at 10° C. After aging at 10° C. for 1 hour, the mixture was added dropwisely to a solution of 60 g of dichloromethane in 100 ml of methanol while the temperature in the reactor was kept at 40° C. After aging at 40° C. for 2 hours, 200 ml of toluene and 400 ml of water were added for extraction. After an aqueous layer was removed, the resultant toluene layer was washed twice with a salt aqueous solution, dehydrated with magnesium sulfate, filtered, and then concentrated to obtain 105 g of concentration residue. The thus-obtained residue was purified by silica gel chromatography using hexane and chloroform as developing solvents. As a result of analysis, the residue was bis(3-thietanylthio)methane (referred to as "compound E" hereinafter). The stability of the thus-obtain compound E was evaluated as ○ (good).

The identification data of compound E is shown below.

TABLE 4

| Elemental analysis | | C | H | S |
|---|---|---|---|---|
| | Theoretical value | 37.5% | 5.4% | 57.1% |
| | Analytical value | 38.2% | 5.6% | 56.2% |
| MS spectrum (EI method) | $M^+$ = 224 | | | |
| IR spectrum | 649 $cm^{-1}$; sulfide 725 $cm^{-1}$; sulfide | | | |
| $^1$H-NMR spectrum (CDCL$_3$) | a; 3.3 ppm (4H) b; 3.5 ppm (4H) c; 3.7 ppm (2H) d; 4.6 ppm (2H) | | | |
| $^{13}$C-NMR spectrum (CDCL$_3$) | 1; 33.8 ppm 2; 34.4 ppm 3; 42.8 ppm | | | |

$$\underset{CH_2}{\overset{CH_2}{S}}\!\!>\!\!\underset{CH_2}{\overset{c,1}{CH}}\!-\!S\!-\!\underset{d,3}{\overset{CH_2}{S}}\!-\!\underset{CH_2}{\overset{a,b,2}{CH}}\!\!<\!\!\underset{}{\overset{CH_2}{S}} \quad (E)$$

EXAMPLE 5

159 g of compound A was charged in a reactor provided with a stirrer and thermometer, and then 300 g of 27% sodium methoxide was added dropwisely to the compound under stirring at 10° C. After aging at 10° C. for 1 hour, the mixture was added dropwisely to a solution of 92 g of bis(chloromethyl) sulfide in 100 ml of methanol while the temperature in the reactor was kept at 40° C. After aging at 40° C. for 2 hours, 200 ml of toluene and 400 ml of water were added for extraction. After an aqueous layer was removed, the resultant toluene layer was washed twice with a salt aqueous solution, dehydrated with magnesium sulfate, filtered, and then concentrated to obtain 164 g of concentration residue. The thus-obtained residue was purified by silica gel chromatography using hexane and chloroform as developing solvents. As a result of analysis, the residue was bis(3-thietanylthiomethyl) sulfide (referred to as "compound F" hereinafter). The stability of the thus-obtain compound F was evaluated as ○ (good).

The identification data of compound F is shown below.

TABLE 5

| Elemental analysis | | C | H | S |
|---|---|---|---|---|
| | Theoretical value | 35.5% | 5.2% | 59.3% |
| | Analytical value | 35.2% | 5.5% | 59.3% |
| MS spectrum (EI method) | $M^+$ = 270 | | | |
| IR spectrum | 643 $cm^{-1}$; sulfide 727 $cm^{-1}$; sulfide | | | |
| $^1$H-NMR spectrum (CDCL$_3$) | a; 3.3 ppm (4H) b; 3.5 ppm (4H) c; 3.8 ppm (4H) d; 4.6 ppm (2H) | | | |
| $^{13}$C-NMR spectrum (CDCL$_3$) | 1; 33.1 ppm 2; 34.3 ppm 3; 42.7 ppm | | | |

TABLE 5-continued

| Elemental analysis | C | H | S |
|---|---|---|---|

Structure (F): thietane-S-CH(CH₂)-S-S-CH₂-CH₂-S-CH(CH₂CH₂)S with labels c,1; a,b,2; d,3

EXAMPLE 6

159 g of compound A was charged in a reactor provided with a stirrer and thermometer, and then 300 g of 27% sodium methoxide was added dropwisely to the compound under stirring at 10° C. After aging at 10° C. for 1 hour, the mixture was added dropwisely to a solution of 123 g of m-xylylene dichloride in 100 ml of methanol while the temperature in the reactor was kept at 40° C. After aging at 40° C. for 2 hours, 200 ml of toluene and 400 ml of water were added for extraction. After an aqueous layer was removed, the resultant toluene layer was washed twice with a salt aqueous solution, dehydrated with magnesium sulfate, filtered and then concentrated to obtain 154 g of concentration residue. The thus-obtained residue was purified by silica gel chromatography using hexane and chloroform as developing solvents. As a result of analysis, the residue was 1,3-bis(3-thietanylthiomethyl) benzene (referred to as "compound G" hereinafter). The stability of the thus-obtain compound G was evaluated as ○ (good).

The identification data of compound G is shown below.

TABLE 6

| Elemental analysis | | C | H | S |
|---|---|---|---|---|
| | Theoretical value | 53.4% | 5.8% | 40.8% |
| | Analytical value | 53.6% | 5.9% | 40.5% |
| MS spectrum (EI method) | M⁺ = 314 | | | |
| IR spectrum | 652 cm⁻¹; sulfide | | | |
| | 711, 795 cm⁻¹; m-benzene ring | | | |
| | 1604 cm⁻¹; benzene ring | | | |
| ¹H-NMR spectrum (CDCL₃) | a; 3.1 ppm (4H)   b; 3.4 ppm (4H) | | | |
| | c; 3.7 ppm (4H)   d; 4.3 ppm (2H) | | | |
| | e; 7.2 ppm (2H)   f; 7.3 ppm (2H) | | | |
| ¹³C-NMR spectrum (CDCL₃) | 1; 34.2 ppm   2; 35.3 ppm | | | |
| | 3; 42.6 ppm   4; 127.5 ppm | | | |
| | 5; 128.9 ppm   6; 138.6 ppm | | | |

Structure (G) with labels c,1; a,b,2; d,3; 5,f; e,4; 6

EXAMPLE 7

159 g of compound A was charged in a reactor provided with a stirrer and thermometer, and then 300 g of 27% sodium methoxide was added dropwisely to the resultant mixture under stirring at 10° C. After aging at 10° C. for 1 hour, the mixture was added dropwisely to a solution of 152 g of 2,5-bis(chloromethyl)-1,4-dithiane in 100 ml of methanol while the temperature in the reactor was kept at 40° C. After aging at 40° C. for 2 hours, 200 ml of toluene and 400 ml of water were added for extraction. After an aqueous layer was removed, the resultant toluene layer was washed twice with a salt aqueous solution, dehydrated with magnesium sulfate, filtered and then concentrated to obtain 182 g of concentration residue. The thus-obtained residue was purified by silica gel chromatography using hexane and chloroform as developing solvents. As a result of analysis, the residue was 2,5-bis(3-thietanylthiomethy)-1,4-dithiane (referred to as "compound H" hereinafter). The stability of the thus-obtain compound H was evaluated as ○ (good).

The identification data of compound H is shown below.

TABLE 7

| Elemental analysis | | C | H | S |
|---|---|---|---|---|
| | Theoretical value | 40.4% | 5.6% | 54.0% |
| | Analytical value | 40.1% | 5.5% | 54.4% |
| MS spectrum (EI method) | M⁺ = 356 | | | |
| IR spectrum | 645 cm⁻¹; sulfide | | | |
| | 724 cm⁻¹; sulfide | | | |
| ¹H-NMR spectrum (CDCL₃) | a; 3.3–3.8 ppm (16H) | | | |
| | b; 4.2–4.5 ppm (4H) | | | |
| ¹³C-NMR spectrum (CDCL₃) | 1; 33.2 ppm   2; 34.4 ppm | | | |
| | 3; 35.2 ppm   4; 41.9 ppm | | | |
| | 5; 42.4 ppm | | | |

Structure (H) with labels a,3; a,2; b,5; b,4; a,1

EXAMPLE 8

159 g of compound A and 0.1 g of 49% caustic soda were charged in a reactor provided with a stirrer and thermometer, and then 138 g of epichlorohydrin was added dropwisely to the resultant mixture under stirring at 5° C. After aging at 10° C. for 2 hours, 200 ml of toluene was added, and then 320 g of 25% caustic soda was dropwisely to the mixture maintained at 20° C. After aging at 20° C. for 2 hours, an aqueous layer was removed, and then the resultant toluene layer was washed twice with a salt aqueous solution, dehydrated with magnesium sulfate, filtered and then concentrated to obtain 238 of concentration residue. The residue was 3-(2,3-epoxypropylthio)thietane (referred to as "compound I" hereinafter).

80 g of thiourea, 63 g of acetic acid and 100 g of water were charged in a reactor provided with a stirrer and thermometer, and then 165 g of compound I was added dropwisely to the resultant mixture under stirring at 20° C. After aging for 3 hours, 100 ml of toluene was added to the mixture, and then 72 g of 25% ammonia water was added dropwisely to the mixture maintained at 15° C. After aging 2 hours, an aqueous layer was removed, and then the resultant toluene layer was washed twice with a salt aqueous solution, dehydrated with magnesium sulfate, filtered and then concentrated. The thus-obtained residue was purified by silica gel chromatography using hexane and chloroform as developing solvents. As a result of analysis, the concentration residue was 3-(2,3-epithiopropyltiho) thietane (referred to as "compound J" hereinafter).

The identification data of compound J is shown below.

TABLE 8

| Elemental analysis | | C | H | S |
|---|---|---|---|---|
| | Theoretical value | 40.5% | 5.6% | 53.9% |
| | Analytical value | 41.6% | 5.2% | 53.2% |
| MS spectrum (EI method) | $M^+ = 178$ | | | |
| IR spectrum | 616 cm$^{-1}$; episulfide | | | |
| | 653 cm$^{-1}$; sulfide | | | |
| $^1$H-NMR spectrum (CDCL$_3$) | a; 2.2 ppm (1H) | b; 2.5 ppm (1H) | | |
| | c; 2.6 ppm (1H) | d; 2.9 ppm (1H) | | |
| | e; 3.0 ppm (1H) | f; 3.3 ppm (2H) | | |
| | g; 3.4 ppm (2H) | h; 4.5 ppm (1H) | | |
| $^{13}$C-NMR spectrum (CDCL$_3$) | 1; 25.8 ppm | 2; 34.1 ppm | | |
| | 3; 34.6 ppm | 4; 37.5 ppm | | |
| | 5; 43.3 ppm | | | |

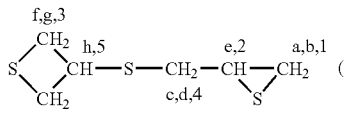

EXAMPLE 9

159 g of compound A, 181 g of allyl bromide and 100 ml of methanol were charged in a reactor provided with a stirrer and thermometer, and then 290 g of 28% sodium methoxide was added dropwisely to the resultant mixture under stirring at 5° C. After aging at 10° C. for 2 hours, 500 ml of toluene and 1000 ml of water were added. After stirring, an aqueous layer was removed, and then the resultant toluene layer was washed twice with a salt aqueous solution, dehydrated with magnesium sulfate, filtered and then concentrated to obtain 198 g of concentration residue. The thus-obtained residue was purified by silica gel chromatography using hexane and chloroform as developing solvents. As a result of analysis, the residue was 3-(allylthio)thietane (referred to as "compound K" hereinafter). The stability of the thus-obtain compound K was evaluated as ○ (good).

The identification data of compound K is shown below.

TABLE 9

| Elemental analysis | | C | H | S |
|---|---|---|---|---|
| | Theoretical value | 49.3% | 6.8% | 43.8% |
| | Analytical value | 50.1% | 6.6% | 43.3% |
| MS spectrum (EI method) | $M^+ = 146$ | | | |
| IR spectrum | 655 cm$^{-1}$; sulfide | | | |
| | 1635 cm$^{-1}$; allyl | | | |
| | 3079 cm$^{-1}$; allyl | | | |
| 1H-NMR spectrum (CDCL$_3$) | a; 3.1 ppm (2H) | b; 3.2 ppm (2H) | | |
| | c; 3.4 ppm (2H) | d; 4.3 ppm (1H) | | |
| | e; 5.1 ppm (2H) | f; 5.8 ppm (1H) | | |
| $^{13}$C-NMR spectrum (CDCL$_3$) | 1; 34.3 ppm | 2; 34.6 ppm | | |
| | 3; 42.3 ppm | 4; 117.1 ppm | | |
| | 5; 134.5 ppm | | | |

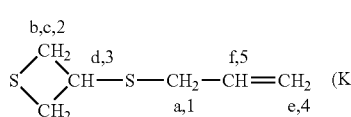

EXAMPLE 10

159 g of compound A and 500 ml of toluene were charged in a reactor provided with a stirrer and thermometer, and then 180 g of 3-chloropropionic chloride and 120 g of pyridine were simultaneously added dropwisely to the resultant mixture under stirring at 35° C. After aging at 40° C. for 2 hours, 1000 ml of water was added to the mixture. After stirring, an aqueous layer was removed, and then the resultant toluene layer was washed twice with water and then dehydrated with magnesium sulfate. The thus-obtained toluene solution contained 3-(3-chloropropionylthio)thietane (referred to as "compound L" hereinafter).

A toluene solution of compound L was charged in a reactor provided with a stirrer and thermometer, and then 150 g of triethylamine was added dropwisely to the solution under stirring at 20° C. After aging at 25° C. for 2 hours, 100 ml of toluene and 500 ml of water were added. After stirring, an aqueous layer was removed, and then the resultant toluene layer was washed twice with water, dehydrated with magnesium sulfate, filtered and then concentrated to obtain 210 g of concentration residue. The thus-obtained residue was purified by silica gel chromatography using hexane and chloroform as developing solvents. As a result of analysis, the residue was 3-(acryloylthio)thietane (referred to as "compound M" hereinafter).

The identification data of compound M is shown below.

TABLE 10

| Elemental analysis | | C | H | O | S |
|---|---|---|---|---|---|
| | Theoretical value | 45.0% | 5.0% | 10.0% | 40.0% |
| | Analytical value | 45.6% | 4.8% | 11.1% | 38.5% |
| MS spectrum (EI method) | $M^+ = 160$ | | | | |
| IR spectrum | 659 cm$^{-1}$; sulfide | | | | |
| | 1613 cm$^{-1}$; acryl | | | | |
| | 1672 cm$^{-1}$; thioester | | | | |
| $^1$H-NMR spectrum (CDCL$_3$) | a; 3.3 ppm (2H) | b; 3.5 ppm (2H) | | | |
| | c; 5.1 ppm (1H) | d; 5.7 ppm (1H) | | | |
| | e; 6.3 ppm (2H) | | | | |
| $^{13}$C-NMR spectrum (CDCL$_3$) | 1; 33.8 ppm | 2; 39.8 ppm | | | |
| | 3; 127.3 ppm | 4; 134.5 ppm | | | |
| | 5; 188.8 ppm | | | | |

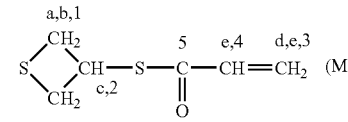

EXAMPLE 11

159 g of compound A and 500 ml of toluene were charged in a reactor provided with a stirrer and thermometer, and then 136 g of methacrylic chloride and 120 g of pyridine were simultaneously added dropwisely to the resultant mixture under stirring at 10° C. After aging at 10° C. for 2 hours, 1000 ml of water was added to the mixture. After stirring, an aqueous layer was removed, and then the resultant toluene layer was washed twice with water, dehydrated with magnesium sulfate, filtered and then concentrated to obtain 232 g of concentration residue. The thus-obtained residue was purified by silica gel chromatography using hexane and chloroform as developing solvents to obtain 124 g of a liquid material. As a result of analysis, the liquid material was 3-(methacyloylthio)thietane (referred to as "compound N" hereinafter).

The identification data of compound N is given blow.

TABLE 11

| Elemental analysis | | C | H | O | S |
|---|---|---|---|---|---|
| | Theoretical value | 48.2% | 5.8% | 9.2% | 36.8% |
| | Analytical value | 48.6% | 5.4% | 9.6% | 36.4% |
| MS spectrum (EI method) | $M^+ = 174$ | | | | |
| IR spectrum | 655 cm$^{-1}$; sulfide 1617 cm$^{-1}$; acryl 1663 cm$^{-1}$; thioester | | | | |
| $^1$H-NMR spectrum (CDCL$_3$) | a; 1.9 ppm (3H) c; 3.5 ppm (2H) e; 5.6 ppm (1H) | b; 3.3 ppm (2H) d; 5.1 ppm (1H) f; 6.1 ppm (1H) | | | |
| $^{13}$C-NMR spectrum (CDCL$_3$) | 1; 17.8 ppm 3; 40.0 ppm 5; 143.2 ppm | 2; 34.1 ppm 4; 123.8 ppm 6; 191.9 ppm | | | |

$$\underset{\text{CH}_2}{\overset{\text{CH}_2}{S}}\underset{d,3}{\overset{b,c,2}{\diagdown}}\text{CH}-\text{S}-\overset{6}{\underset{\|}{C}}-\overset{a,1}{\underset{5}{C}}=\text{CH}_2 \quad (N)$$

EXAMPLE 12

106 g of compound A, 500 ml of toluene, and 0.5 g of triethylamine were charged in a reactor provided with a stirrer and thermometer, and then 160 g of compound M was added dropwisely to the resultant mixture under stirring at 10° C. After aging at 10° C. for 2 hours, 1000 ml of a sodium bicarbonate aqueous solution was added to the mixture. After stirring, an aqueous layer was removed, and then the resultant toluene layer was washed twice with water, dehydrated with magnesium sulfate, filtered and then concentrated to obtain 220 g of concentration residue. The thus-obtained residue was purified by silica gel chromatography using hexane and chloroform as developing solvents to obtain 184 g of a liquid material. As a result of analysis, the liquid material was 1,3-bis(3-thietanylthio)propane-1-one (referred to as "compound O" hereinafter). The stability of compound O was evaluated as ○ (good).

The identification data of compound O is shown below.

TABLE 12

| Elemental analysis | | C | H | O | S |
|---|---|---|---|---|---|
| | Theoretical value | 40.6% | 5.3% | 6.0% | 48.1% |
| | Analytical value | 40.4% | 5.2% | 6.8% | 47.6% |
| MS spectrum (EI method) | $M^+ = 266$ | | | | |
| IR spectrum | 658 cm$^{-1}$; sulfide 1690 cm$^{-1}$; thioester | | | | |
| $^1$H-NMR spectrum (CDCL$_3$) | a; 2.8 ppm (2H) c; 3.2–3.5 ppm (4H) e; 4.4 ppm (1H) | b; 2.8 ppm (2H) d; 3.4–3.5 ppm (4H) f; 5.1 ppm (1H) | | | |
| $^{13}$C-NMR spectrum (CDCL$_3$) | 1; 25.7 ppm 3; 34.3 ppm 5; 43.2 ppm 7; 195.8 ppm | 2; 33.8 ppm 4; 40.0 ppm 6; 44.0 ppm | | | |

TABLE 12-continued

| Elemental analysis | C | H | O | S |
|---|---|---|---|---|

$$\underset{\text{CH}_2}{\overset{d,2}{\overset{\text{CH}_2}{\diagdown}}}\underset{f,4}{\overset{}{\diagup}}\text{CH}-\text{S}-\overset{7}{\underset{\|}{\underset{O}{C}}}-\overset{a,6}{\text{CH}_2}-\text{CH}_2-\text{S}-\underset{e,5}{\overset{c,3}{\diagup}}\text{CH}\underset{\text{CH}_2}{\overset{\text{CH}_2}{\diagdown}}S \quad (O)$$

EXAMPLE 13

106 g of compound A, 500 ml of toluene, and 0.5 g of triethylamine were charged in a reactor provided with a stirrer and thermometer, and then 174 g of compound N was added dropwisely to the resultant mixture under stirring at 10° C. After aging at 10° C. for 2 hours, 1000 ml of a sodium bicarbonate aqueous solution was added to the mixture. After stirring, an aqueous layer was removed, and then the resultant toluene layer was washed twice with water, dehydrated with magnesium sulfate, filtered and then concentrated to obtain 224 g of concentration residue. The thus-obtained residue was purified by silica gel chromatography using hexane and chloroform as developing solvents to obtain 196 g of a liquid material. As a result of analysis, the liquid material was 1,3-bis(3-thietanylthio)-2-methylpropane-1-one (referred to as "compound P" hereinafter). The stability of compound P was evaluated as ○ (good).

The identification data of compound P is shown below.

TABLE 13

| Elemental analysis | | C | H | O | S |
|---|---|---|---|---|---|
| | Theoretical value | 42.8% | 5.8% | 5.7% | 45.7% |
| | Analytical value | 42.4% | 5.6% | 5.7% | 46.3% |
| MS spectrum (EI method) | $M^+ = 280$ | | | | |
| IR spectrum | 657 cm$^{-1}$; sulfide 1686 cm$^{-1}$; thioester | | | | |
| $^1$H-NMR spectrum (CDCL$_3$) | a; 1.2 ppm (3H) c; 2.7 ppm (1H) e; 3.5 ppm (4H) g; 5.1 ppm (1H) | b; 2.6–2.9 ppm (2H) d; 3.2–3.4 ppm (4H) f; 4.4 ppm (1H) | | | |
| $^{13}$C-NMR spectrum (CDCL$_3$) | 1; 17.3 ppm 3; 34.0 ppm 5; 40.0 ppm 7; 48.8 ppm | 2; 33.8 ppm 4; 34.4 ppm 6; 43.6 ppm 8; 200.4 ppm | | | |

$$\underset{\text{CH}_2}{\overset{e,2}{\overset{\text{CH}_2}{\diagdown}}}\underset{g,5}{\overset{}{\diagup}}\text{CH}-\text{S}-\overset{8}{\underset{\|}{\underset{O}{C}}}-\overset{a,1}{\underset{c}{\text{CH}_3}}\overset{}{\underset{b,3}{\text{CH}}}-\text{CH}_2-\text{S}-\underset{f,6}{\overset{d,4}{\diagup}}\text{CH}\underset{\text{CH}_2}{\overset{\text{CH}_2}{\diagdown}}S \quad (P)$$

EXAMPLE 14

106 g of compound A was charged in a reactor provided with a stirrer and thermometer, and then 267 g of 15% caustic soda aqueous solution was added dropwisely to the compound at 10° C. Then, 125 g of ethyl chloroacetate was added dropwisely to the resultant mixture at 10° C. After aging at room temperature for 1 hour, the mixture was separated into layers by still standing. After separation, a lower layer was taken out, and dissolved in 500 ml of MeOH, and then 63 g of hydrazine hydrate was added dropwisely to the resultant solution at 10° C. After aging at 40° C., the mixture was further stirred at room temperature over one night. The precipitated crystal was filtered off, and then the resulting filter cake was dried to obtain 152 g of a white crystal. 150 g of the thus-obtained white crystal was added to 250 g of 15% hydrochloric acid, and then 300 ml of toluene was added to the resultant mixture. Then, 300 g of a 30% sodium nitrite aqueous solution was added dropwisely to the mixture at 5° C., and then aged. After aging, an organic layer was taken out, dehydrated with magnesium sulfate at 5° C., and then filtered, and then added to a toluene solution at 80° C. After dropping, the internal temperature of the reactor was increased to 100° C. for aging. After aging, the toluene solution was concentrated to obtain 89 g of concentration residue. The thus-obtained concentration residue was simply distilled to recover 72 g of distillate of 88° C. under 100 Pa. As a result of analysis of the recovered distillate, the distillate was 3-(isocyanatomethylthio)thietane (referred to as "compound Q" hereinafter). The stability of compound Q was evaluated as ○ (good).

The identification data of compound Q is shown below.

TABLE 14

| Elemental analysis | | C | H | N | O | S |
|---|---|---|---|---|---|---|
| | Theoretical value | 37.2% | 4.4% | 8.7% | 9.9% | 39.8% |
| | Analytical value | 37.6% | 4.1% | 8.9% | 9.2% | 40.2% |
| MS spectrum (EI method) | M⁺ = 161 | | | | | |
| IR spectrum | 2241 cm⁻¹; isocyanate | | | | | |
| ¹H-NMR spectrum (CDCL₃) | a; 3.3–3.5 ppm (4H) b; 4.3 ppm (2H) c; 4.6 ppm (1H) | | | | | |
| ¹³C-NMR spectrum (CDCL₃) | 1; 34.4 ppm 2; 42.9 ppm 3; 44.3 ppm | | | | | |

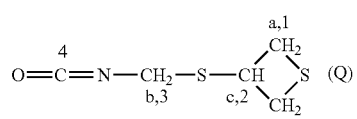

EXAMPLE 15

106 g of compound A was charged in a reactor provided with a stirrer and thermometer, and then 534 g of a 15% caustic soda aqueous solution was added dropwisely to the compound at 10° C. Then, an aqueous solution of 127 g of chloroethylamine hydrochloride in 200 g of water was added dropwisely to the mixture at 10° C., and aged at 30° C. for 2 hours. After still standing, 158 g of the separated lower layer was recovered. Then, the recovered lower layer was simply distilled to recover 109 g of a distillate of 89° C. under 60 Pa. As a result of analysis, the recovered distillate was 3-(aminoethylthio)thietane (referred to as "compound R" hereinafter). The stability of compound R was evaluated as ○ (good).

The identification data of compound R is shown below.

TABLE 15

| Elemental analysis | | C | H | N | S |
|---|---|---|---|---|---|
| | Theoretical value | 40.2% | 7.4% | 9.4% | 43.0% |
| | Analytical value | 40.6% | 7.9% | 10.0% | 41.5% |

TABLE 15-continued

| Elemental analysis | | C | H | N | S |
|---|---|---|---|---|---|
| MS spectrum (EI method) | M⁺ = 149 | | | | |
| IR spectrum | 1590 cm⁻¹; amine 3361 cm⁻¹; amine | | | | |
| ¹H-NMR spectrum (CDCL₃) | a; 1.3 ppm (2H) c; 2.9 ppm (2H) e; 4.4 ppm (1H) | b; 2.7 ppm (2H) d; 3.2–3.5 ppm (4H) | | | |
| ¹³C-NMR spectrum (CDCL₃) | 1; 34.6 ppm 3; 41.7 ppm | 2; 35.2 ppm 4; 43.0 ppm | | | |

$$H_2N\underset{a}{-}\underset{c,3}{CH_2}-\underset{b,2}{CH_2}-S-\underset{e,4}{CH}\underset{CH_2}{\overset{CH_2}{\diagup}}S \quad (R)$$

EXAMPLE 16

75 g of compound R and 70 g of a 30% caustic soda aqueous solution were charged in a reactor provided with a stirrer and thermometer, and then 46 g of carbon disulfide was added dropwisely to the resultant mixture at 40° C. After aging at 70° C. for 1 hour, 200 ml of toluene was added to the mixture. Then, 57 g of methyl chloroformate was added dropwisely to the mixture at 50° C., and then aged for 2 hours. Then, the reaction solution was allowed to stand, and an organic layer was taken out. The organic layer was dehydrated with magnesium sulfate, filtered and then concentrated to obtain 92 g of concentration residue. The thus-obtained residue was simply distilled to recover a distillate of 155° C. under 130 Pa. As a result of analysis, the recovered distillate was 3-(isothiocyanatoethylthio)thietane (referred to as "compound S" hereinafter). The stability of compound S was evaluated as ○ (good).

The identification data of compound S is shown below.

TABLE 16

| Elemental analysis | | C | H | N | S |
|---|---|---|---|---|---|
| | Theoretical value | 37.7% | 4.7% | 7.3% | 50.3% |
| | Analytical value | 36.2% | 4.8% | 7.6% | 51.4% |
| MS spectrum (EI method) | M⁺ = 191 | | | | |
| IR spectrum | 2183–2082 cm⁻¹; isothiocyanate | | | | |
| ¹H-NMR spectrum (CDCL₃) | a; 2.6 ppm (2H) c; 3.3 ppm (2H) | b; 3.2–3.4 ppm (4H) d; 4.3 ppm (1H) | | | |
| ¹³C-NMR spectrum (CDCL₃) | 1; 31.4 ppm 3; 43.5 ppm 5; 133.0 ppm | 2; 34.7 ppm 4; 45.6 ppm | | | |

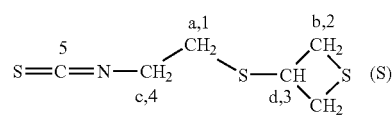

EXAMPLE 17

30 g of compound C, 0.03 g of Viosorb 583 (produced by Kyodo Chemical Co., Ltd.) as an ultraviolet absorber, and 0.15 g of dimethyltin dichloride as a catalyst were charged in a beaker at room temperature of 20° C., and then stirred for 30 minutes to sufficiently dissolve a powder. The resultant mixture was filtered, and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain and was colorless.

As a result of measurement of the optical physical properties and specific gravity of the obtained resin, the refractive index ne=1.701 and Abbe's number ve=36, and specific gravity=1.41.

EXAMPLE 18

30 g of compound D, 0.03 g of Viosorb 583 (produced by Kyodo Chemical Co., Ltd.) as an ultraviolet absorber, and 0.15 g of dimethyltin dichloride as a catalyst were charged in a beaker at room temperature of 20° C., and then stirred for 30 minutes to sufficiently dissolve a powder. The resultant mixture was filtered, and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.739 and Abbe's number ve=33, and specific gravity=1.47.

EXAMPLE 19

30 g of compound D, 0.03 g of Viosorb 583 (produced by Kyodo Chemical Co., Ltd.) as an ultraviolet absorber, and 0.09 g of trifluoroacetic acid as a catalyst were charged in a beaker at room temperature of 20° C., and then stirred for 30 minutes to sufficiently dissolve a powder. The resultant mixture was filtered, and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.738 and Abbe's number ve=33, and specific gravity=1.47.

EXAMPLE 20

30 g of compound D, 0.03 g of Viosorb 583 (produced by Kyodo Chemical Co., Ltd.) as an ultraviolet absorber, and 0.15 g of trifluoromethanesulfonic anhydride as a catalyst were charged in a beaker at room temperature of 20° C. in a nitrogen atmosphere, and then stirred for 30 minutes to sufficiently dissolve a powder. The resultant mixture was filtered, and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.737 and Abbe's number ve=33, and specific gravity=1.47.

EXAMPLE 21

30 g of compound D, 0.03 g of Viosorb 583 (produced by Kyodo Chemical Co., Ltd.) as an ultraviolet absorber, and 0.15 g of ethyl trifluoromethanesulfonate as a catalyst were charged in a beaker at room temperature of 20° C. in a nitrogen atmosphere, and then stirred for 30 minutes to sufficiently dissolve a powder. The resultant mixture was filtered, and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.737 and Abbe's number ve=33, and specific gravity=1.47.

EXAMPLE 22

30 g of compound D and 0.03 g of Viosorb 583 (produced by Kyodo Chemical Co., Ltd.) as an ultraviolet absorber were stirred in a beaker at room temperature of 20° C. to form a solution, and then 0.15 g of $BF_3$.diethyl etherate was added as a catalyst to the solution in a nitrogen atmosphere and then sufficiently mixed by stirring. The resultant mixture was filtered to remove an insoluble material, and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.739 and Abbe's number ve=33, and specific gravity=1.47.

EXAMPLE 23

30 g of compound D and 0.03 g of Viosorb 583 (produced by Kyodo Chemical Co., Ltd.) as an ultraviolet absorber were stirred in a beaker at room temperature of 20° C. to form a solution, and then 0.15 g of BF$_3$.THF complex was added as a catalyst to the solution in a nitrogen atmosphere and then sufficiently mixed by stirring. The resultant mixture was filtered to remove an insoluble material and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.739 and Abbe's number ve=33, and specific gravity=1.47.

EXAMPLE 24

30 g of compound D and 0.03 g of Viosorb 583 (produced by Kyodo Chemical Co., Ltd.) as an ultraviolet absorber were stirred in a beaker at room temperature of 20° C. to form a solution, and then 0.15 g of BF$_3$.t-butyl methyl ether complex was added as a catalyst to the solution in a nitrogen atmosphere and then sufficiently mixed by stirring. The resultant mixture was filtered to remove an insoluble material and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.739 and Abbe's number ve=33, and specific gravity=1.47.

EXAMPLE 25

3 g of 4,8-, 4,7- or 5,7-dimercaptomethyl-1,11-mercapto-3,6,9-trithiaundecane as an additive and 0.15 g of BF$_3$.THF complex as a catalyst were mixed in a beaker at room temperature of 20° C. in a nitrogen atmosphere, and a solution formed by stirring 30 g of compound D and 0.03 g of Viosorb 583 (produced by Kyodo Chemical Co., Ltd.) as an ultraviolet absorber was added to the resultant mixture and then sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.735 and Abbe's number ve=33, and specific gravity=1.47.

EXAMPLE 26

3 g of 1,1,3,3-tetrakis(mercaptomethylthio)propane as an additive and 0.15 g of BF$_3$.THF complex as a catalyst were mixed in a beaker at room temperature of 20° C. in a nitrogen atmosphere, and a solution formed by stirring 30 g of compound D and 0.03 g of Viosorb 583 (produced by Kyodo Chemical Co., Ltd.) as an ultraviolet absorber was added to the resultant mixture and then sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.736 and Abbe's number ve=33, and specific gravity=1.47.

EXAMPLE 27

3 g of 1,1,3,3-tetrakis(mercaptomethylthio)propane as an additive, 30 g of compound D, and 0.03 g of Viosorb 583 (produced by Kyodo Chemical Co., Ltd.) as an ultraviolet absorber were stirred in a beaker at room temperature of 20° C. to form a solution, and then 0.15 g of BF$_3$.THF complex was added as a curing catalyst and mixed with the solution in a nitrogen atmosphere. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.736 and Abbe's number ve=33, and specific gravity=1.47.

EXAMPLE 28

1.5 g of 1,1,3,3-tetrakis(mercaptomethylthio)propane as an additive and 0.15 9 of BF$_3$.THF complex as a catalyst were mixed in a beaker at room temperature of 20° C. in a nitrogen atmosphere, and then a solution formed by stirring 30 g of compound D and 0.03 g of Viosorb 583 (produced by Kyodo Chemical Co., Ltd.) as an ultraviolet absorber was added to the resultant mixture and sufficiently mixed by stirring. Although no insoluble material was observed. in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.738 and Abbe's number ve=33, and specific gravity=1.47.

EXAMPLE 29

1.5 g of 1,1,3,3-tetrakis(mercaptomethylthio)propane as an additive and 0.15 g of $BF_3$.THF complex as a catalyst were mixed in a beaker at room temperature of 20° C. in a nitrogen atmosphere, and then a solution formed by stirring 30 g of compound E and 0.03 g of Viosorb 583 (produced by Kyodo Chemical Co., Ltd.) as an ultraviolet absorber was added to the resultant mixture and sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.721 and Abbe's number ve=35, and specific gravity=1.44.

EXAMPLE 30

1.5 g of 1,1,3,3-tetrakis(mercaptomethylthio)propane as an additive and 0.15 g of $BF_3$.THF complex as a catalyst were mixed in a beaker at room temperature of 20° C. in a nitrogen atmosphere, and then a solution formed by stirring 30 g of compound F and 0.03 g of Viosorb 583 (produced by Kyodo Chemical Co., Ltd.) as an ultraviolet absorber was added to the resultant mixture and sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.734 and Abbe's number ve=34, and specific gravity=1.45.

EXAMPLE 31

1.5 g of 1,1,3,3-tetrakis(mercaptomethylthio)propane as an additive and 0.15 g of $BF_3$.THF complex as a catalyst were mixed in a beaker at room temperature of 20° C. in a nitrogen atmosphere, and then a solution formed by stirring 30 g of compound G and 0.03 g of Viosorb 583 (produced by Kyodo Chemical Co., Ltd.) as an ultraviolet absorber was added to the resultant mixture and sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.698 and Abbe's number ve=30, and specific gravity=1.39.

EXAMPLE 32

1.5 g of 1,1,3,3-tetrakis(mercaptomethylthio)propane as an additive and 0.15 g of $BF_3$.THF complex as a catalyst were mixed in a beaker at room temperature of 20° C. in a nitrogen atmosphere, and then a solution formed by stirring 30 g of compound H and 0.03 g of Viosorb 583 (produced by Kyodo Chemical Co., Ltd.) as an ultraviolet absorber was added to the resultant mixture and sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.702 and Abbe's number ve=35, and specific gravity=1.41.

EXAMPLE 33

1.5 g of 1,1,3,3-tetrakis(mercaptomethylthio)propane as an additive and 0.15 g of $BF_3$.THF complex as a catalyst were mixed in a beaker at room temperature of 20° C. in a nitrogen atmosphere, and then a solution formed by stirring 30 g of compound J and 0.03 g of Viosorb 583 (produced by Kyodo Chemical Co., Ltd.) as an ultraviolet absorber was added to the resultant mixture and sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed.

Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.703 and Abbe's number ve=36, and specific gravity=1.41.

EXAMPLE 34

0.15 g of 2-hydroxy-2-methyl-1-phenylpropane-1-one was added as a photopolymerization initiator to 30 g of compound M in a beaker at room temperature of 20° C. in a nitrogen atmosphere, and then sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and polymerized by irradiation with ultraviolet rays for 300 seconds using a metal halide lamp (100 W/cm). After the temperature was decreased to near room temperature after polymerization, the glass mold was released to obtain a resin. The thus-obtained resin had excellent transparency and good appearance with no strain.

As a result of measurement of the optical physical properties and specific gravity of the obtained resin, the refractive index ne=1.661 and Abbe's number ve=35, and specific gravity=1.36.

EXAMPLE 35

0.15 g of 2-hydroxy-2-methyl-1-phenylpropane-1-one was added as a photopolymerization initiator to 30 g of compound N in a beaker at room temperature of 20° C. in a nitrogen atmosphere, and then sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and polymerized by irradiation with ultraviolet rays for 300 seconds using a metal halide lamp (100 W/cm). After the temperature was decreased to near room temperature after polymerization, the glass mold was released to obtain a resin. The thus-obtained resin had excellent transparency and good appearance with no strain.

As a result of measurement of the optical physical properties and specific gravity of the obtained resin, the refractive index ne=1.648 and Abbe's number ve=36, and specific gravity=1.34.

EXAMPLE 36

1.5 g of 1,1,3,3-tetrakis(mercaptomethylthio)propane as an additive and 0.15 g of $BF_3$.THF complex as a catalyst were mixed in a beaker at room temperature of 20° C. in a nitrogen atmosphere, and then a solution formed by stirring 30 g of compound O and 0.03 g of Viosorb 583 (produced by Kyodo Chemical Co., Ltd.) as an ultraviolet absorber was added to the resultant mixture and sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.684 and Abbe's number ve=36, and specific gravity=1.38.

EXAMPLE 37

1.5 g of 1,1,3,3-tetrakis(mercaptomethylthio)propane as an additive and 0.15 g of $BF_3$.THF complex as a catalyst were mixed in a beaker at room temperature of 20° C. in a nitrogen atmosphere, and then a solution formed by stirring 30 g of compound P and 0.03 g of Viosorb 583 (produced by Kyodo Chemical Co., Ltd.) as an ultraviolet absorber was added to the resultant mixture and sufficiently mixed by stirring. Although no insoluble material was observed in the resultant mixture, the mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.677 and Abbe's number ve=37, and specific gravity=1.35.

EXAMPLE 38

14.0 g of compound Q was added to a mixture of 16.0 g of 4,8-, 4,7- or 5,7-dimercaptomethyl-1,11-mercapto-3,6,9-trithiaundecane, 0.015 g of dibutyltin dichloride and 0.2 g of $BF_3$.diethyl etherate as a curing catalyst, 0.03 g of Zelec UN (acidic phosphate) as an internal mold releasing agent, and 0.03 g of Viosorb 583 (produced by Kyodo Chemical Co., Ltd.) as an ultraviolet absorber in a beaker at room temperature or 20° C. and sufficiently mixed by stirring. After the mixture was filtered to remove an insoluble material, the mixture was sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.696 and Abbe's number ve=35, and specific gravity=1.43.

EXAMPLE 39

14.2 g of compound Q was added to a mixture of 15.8 g of 1,1,3,3-tetrakis(mercaptomethylthio)propane, 0.015 g of dibutyltin dichloride and 0.2 g of $BF_3$.diethyl etherate as a curing catalyst, 0.03 g of Zelec UN (acidic phosphate) as an internal mold releasing agent, and 0.03 g of Viosorb 583 (produced by Kyodo Chemical Co., Ltd.) as an ultraviolet absorber in a beaker at room temperature or 20° C. and sufficiently mixed by stirring., After the mixture was filtered to remove an insoluble material, the mixture was sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.726 and Abbe's number ve=32, and specific gravity=1.49.

EXAMPLE 40

15.5 g of compound S was added to a mixture of 14.5 g of 1,1,3,3-tetrakis(mercaptomethylthio)propane, 0.03 g of dibutyltin dichloride and 0.2 g of $BF_3$.diethyl etherate as a curing catalyst, 0.03 g of Zelec UN (acidic phosphate) as an internal mold releasing agent, and 0.03 g of Viosorb 583 (produced by Kyodo Chemical Co., Ltd.) as an ultraviolet absorber in a beaker at room temperature or 20° C. and sufficiently mixed by stirring. After the mixture was filtered to remove an insoluble material, the mixture was sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin had excellent transparency and good appearance with no strain.

As a result of measurement of the optical physical properties and specific gravity of the obtained resin, the refractive index ne=1.753 and Abbe's number ve=26, and specific gravity=1.52.

EXAMPLE 41

The lens obtained in each of Examples 23, 25, 26, 38 and 39 was tested with respect to impact resistance. As a result, the impact resistance of any of the lenses was evaluated as ○ (good).

COMPARATIVE EXAMPLE 1

Bis(2,3-epithiopropyl) sulfide (referred to as "compound T" hereinafter) was synthesized as a polyepisulfide compound by the method disclosed in Japanese Unexamined Patent Application Publication No. 9-110979, and then tested with respect to stability. As a result, the stability was evaluated as × (not good). 30 g of compound E, 0.03 g of Viosorb 583 (produced by Kyodo Chemical Co., Ltd.) as an ultraviolet absorber, and 0.15 g of tetrabutylphosphonium bromide as a catalyst were charged in a beaker at room temperature of 20° C., and then stirred for 30 minutes to sufficiently dissolve a powder. The mixture was filtered and then sufficiently degassed under a reduced pressure of 1.3 kPa or less. The degassed solution was injected into a mold formed by a glass mold and a tape, and placed in a polymerization furnace in which the temperature could be programmed. Then, the temperature was gradually increased from 30° C. to 120° C. to perform polymerization for 20 hours. After the temperature was decreased to near room temperature, the glass mold was released to obtain a resin. The thus-obtained resin was transparent.

As a result of measurement of the optical physical properties and specific gravity of the obtained resin, the refractive index ne=1.704 and Abbe's number ve=36, and specific gravity=1.41.

As a result of an impact resistance test of the obtained lens, the impact resistance was evaluated as × (not good) and inferior to that evaluated in Example 41.

INDUSTRIAL APPLICABILITY

According to the present invention, an optical material used in a high-refractive index field, particularly, a useful compound is obtained as a substitute with a higher refractive index for a resin produced by using a polyepisulfide compound as a raw material. The optical material has high preservation stability and thus has excellent handleability. Furthermore, a resin produced by using the compound has high optical physical properties and high impact resistance, and thus contributes to an increase in refractive index and a decrease in thickness, particularly, in the field of eyeglasses.

The invention claimed is:

1. A sulfur-containing compound having a structure represented by formula (1):

(wherein R1 represents a hydrogen atom, a reactive terminal group, a straight, branched or cyclic alkyl group having 1 to 10 carbon atoms with a reactive terminal group or its thia derivative, an aryl group with a reactive terminal group, or an aralkyl group with a reactive terminal group; Y represents a sulfur atom, a selenium atom, or a tellurium atom; R represents a substituted or unsubstituted bivalent hydrocarbon group having 1 to10 carbon atoms, which may be thianated; n represents an integer of 0 to 3; and $X_1$ is substituted for any one of groups R2 to R7 of a partial structure represented by formula (2) in which the groups R2 to R7 other than the group substituted by $X_1$ are independently a hydrogen atom or a substituted or unsubstituted monovalent hydrocarbon group having 1 to10 carbon atoms

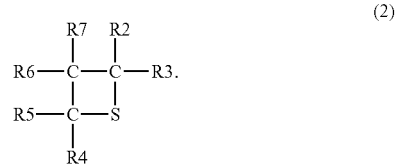

2. The sulfur-containing compound according to claim 1, the compound having a structure represented by formula (3):

(3)

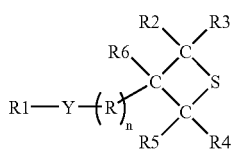

(wherein R1 represents a hydrogen atom, a reactive terminal group, a straight, branched or cyclic alkyl group having 1 to 10 carbon atoms with a reactive terminal group or its thia derivative, an aryl group with a reactive terminal group, or an aralkyl group with a reactive terminal group; R2 to R6 independently represent a hydrogen atom or a substituted or unsubstituted monovalent hydrocarbon group having 1 to 10 carbon atoms; R represents a substituted or unsubstituted divalent hydrocarbon group having 1 to 10 carbon atoms, which may be thianated; n represents an integer of 0 to 3; and Y represents a sulfur atom, a selenium atom, or a tellurium atom.

3. The sulfur-containing compound according to claim 1, the compound having a structure represented by formula (4):

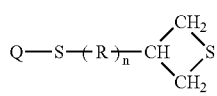

(4)

(wherein Q represents a hydrogen atom, a straight, branched or cyclic alkyl group having 1 to 10 carbon atoms with a reactive terminal group or its thia derivative, an aryl group with a reactive terminal group, or an aralkyl group with a reactive terminal group; R represents a substituted or unsubstituted divalent hydrocarbon group having 1 to 10 carbon atoms, which may be thianated; and n represents an integer of 0 to 3).

4. The sulfur-containing compound according to claim 1, the compound being selected from the group consisting of 3-mercaptothietane, 3-(acryloylthio)thietane, 3-(methacryloylthio)thietane, 3-(2,3-epithiopropylthio)thietane, 3-(allylthio)thietane, 3-(isocyanatomethylthio)thietane, 3-(aminoethylthio)thietane, and 3-(isothiocyanatoethylthio)thietane.

5. The sulfur-containing compound according to claim 1, the compound having a structure represented by formula (5):

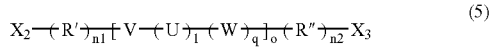

(5)

(wherein R' and R" independently represent a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; each of V and W represents a sulfur atom, a selenium atom, or a tellurium atom; l represents an integer of 0 to 2; o represents an integer of 1 to 4; n1 and n2 independently represent an integer of 0 to 3; q represents an integer of 0 or 1; $X_2$ is substituted for any one of groups R9 to R14 of a partial structure represented by formula (6), and $X_3$ is substituted for any one of groups R15 to R20 of the partial structure represented by formula (6) in which the groups R9 to R20 other than the groups substituted by $X_2$ and $X_3$ are independently a hydrogen atom or a substituted or unsubstituted monovalent hydrocarbon group having 1 to 10 carbon atoms)

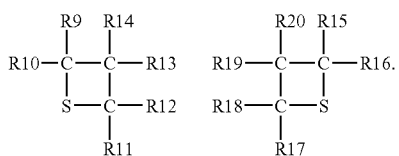

(6)

6. The sulfur-containing compound according to claim 1, the compound being represented by formula (7):

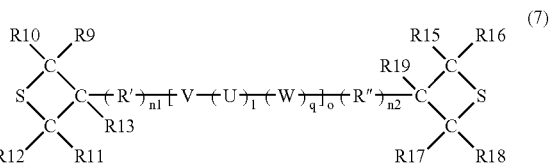

(7)

(wherein R9 to R19 independently represent a hydrogen atom, a substituted or unsubstituted monovalent hydrocarbon group having 1 to 10 carbon atoms; R' and R" independently represent a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; each of V and W represents an oxygen atom, a sulfur atom, a selenium atom, or a tellurium atom; l represents an integer of 0 to 2; o represents an integer of 1 to 4; n1 and n2 independently represent an integer of 0 to 3; and q represents an integer of 0 or 1).

7. The sulfur-containing compound according to claim 1, the compound being represented by formula (8):

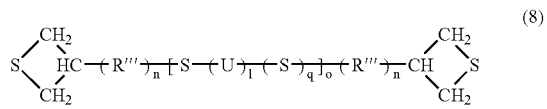

(8)

(wherein R''' represents a substituted or unsubstituted divalent hydrocarbon group having 1 to 10 carbon atoms, which may be thianated; U represents a substituted or unsubstituted straight, branched or cyclic alkylene group having 1 to 10 carbon atoms, an arylene group, or an aralkylene group, which may be thianated; l represents an integer of 0 to 2; o represents an integer of 1 to 4; n represents an integer of 0 to 3; and q represents an integer of 0 or 1).

8. The sulfur-containing compound according claim 1, the compound being selected from the group consisting of bis(3-thietanyl) disulfide, bis(3-thietanyl) sulfide, bis(3-thietanylthio) methane, bis(3-thietanylthiomethyl) sulfide, 1,4-bis(3-thietanylthiomethyl) benzene, 1,3-bis(thietanylthiomethyl) benzene, 1,2-bis(thietanylthiomethyl) benzene, 2,5-bis(3-thietanylthiomethyl)-1,4-dithiane, 1,3-bis(3-thietanylthio)propoane-1-one, and 1,3-bis(3-thietanylthio) propane-1-one-2-methyl.

9. A method for producing the sulfur-containing compound according to claim 1, the compound being derived from at least one of compound selected from the group consisting of 3-thiethanol, 3-halogenothietane and 3-mercaptothietane.

10. A polymerizable composition containing the compound according to claim 1.

11. A resin produced by curing the polymerizable composition according to claim 10.

12. An optical material comprising the resin according to claim 11.

13. A method for producing a resin comprising cast-polymerizing the polymerizable composition according to claim 10.

14. A method for producing a resin comprising curing a resin by using the polymerizable composition according to claim 10 as a curing catalyst, and at least one compound selected from boron trihalides and complexes thereof, trihalogenomethane sulfonic acids and esters and anhydrides thereof.

15. A method for producing a resin comprising curing a resin by using the polymerizable composition according to claim 10 as a resin modifier, and at least one compound selected from compounds each having at least one SH group and/or NH group and/or NH2 group.

* * * * *

UNITED STATES PATENT AND TRADEMARK OFFICE
CERTIFICATE OF CORRECTION

PATENT NO. : 7,132,501 B2
APPLICATION NO. : 10/504190
DATED : November 7, 2006
INVENTOR(S) : Seiichi Kobayashi et al.

It is certified that error appears in the above-identified patent and that said Letters Patent is hereby corrected as shown below:

On the Title Page: Item (56) insert

NON-PATENT LITERATURE DOCUMENTS

M. SANDER, "Preparation of arylthioglycidic ethers and 3-aryloxythietanes," Monatsh. Chem. 1965, 96(3), 896-908 (German). *Chemical Abstracts*, Vol. 63, IV, October 11, 1965, Abstract No. 11468d-h, 11469a-b M.A. ALLAKHVERDIEV et al., "Synthesis and properties of bis(thietane) alkanedicarboxylates," Khimiya Geterotsikilicheskikh Soedinenii. 1988, (12), 1619-1620 (Russian). *Chemical Abstracts*, Vol. 111, No. 17, October 23, 1989, Abstract No. 153540m Signed and Sealed this Twenty-fourth Day of April, 2007

JON W. DUDAS
*Director of the United States Patent and Trademark Office*